United States Patent
Craig

(10) Patent No.: US 9,433,563 B2
(45) Date of Patent: Sep. 6, 2016

(54) DENTAL COMPOSITIONS COMPRISING A FATTY MONO(METH)ACRYLATE

(76) Inventor: Bradley D. Craig, Lake Elmo, MN (US)

( * ) Notice: Subject to any disclaimer, the term of this patent is extended or adjusted under 35 U.S.C. 154(b) by 194 days.

(21) Appl. No.: 14/111,376

(22) PCT Filed: Jun. 27, 2012

(86) PCT No.: PCT/US2012/044290
§ 371 (c)(1),
(2), (4) Date: Oct. 11, 2013

(87) PCT Pub. No.: WO2013/003396
PCT Pub. Date: Jan. 3, 2013

(65) Prior Publication Data
US 2014/0099271 A1 Apr. 10, 2014

Related U.S. Application Data

(60) Provisional application No. 61/502,500, filed on Jun. 29, 2011.

(51) Int. Cl.
| | | |
|---|---|---|
| A61K 6/00 | (2006.01) | |
| A61Q 11/00 | (2006.01) | |
| A61K 6/087 | (2006.01) | |
| A61K 6/083 | (2006.01) | |

(52) U.S. Cl.
CPC ............ *A61K 6/0047* (2013.01); *A61K 6/083* (2013.01); *A61K 6/087* (2013.01); *A61Q 11/00* (2013.01)

(58) Field of Classification Search
USPC ............................................ 106/35; 523/115
See application file for complete search history.

(56) References Cited

U.S. PATENT DOCUMENTS

| | | | |
|---|---|---|---|
| 4,503,169 A | | 3/1985 | Randklev |
| 4,782,100 A | | 11/1988 | Iwamoto |
| 5,037,473 A | * | 8/1991 | Antonucci et al. ............ 106/35 |
| 5,130,347 A | | 7/1992 | Mitra |
| 5,154,762 A | | 10/1992 | Mitra |
| 5,501,727 A | | 3/1996 | Wang |
| 5,545,676 A | | 8/1996 | Palazzotto |
| 5,962,550 A | | 10/1999 | Akahane |
| 6,057,383 A | | 5/2000 | Volkel |
| 6,126,922 A | | 10/2000 | Rozzi |
| 6,284,898 B1 | | 9/2001 | Moszner |
| 6,316,519 B1 | * | 11/2001 | Berge et al. ................. 522/182 |
| 6,387,981 B1 | | 5/2002 | Zhang |
| 6,572,693 B1 | | 6/2003 | Wu |
| 6,670,436 B2 | | 12/2003 | Burgath |
| 6,730,156 B1 | | 5/2004 | Windisch |
| 6,794,520 B1 | | 9/2004 | Moszner |
| 6,799,969 B2 | | 10/2004 | Sun |
| 7,090,721 B2 | | 8/2006 | Craig |
| 7,090,722 B2 | | 8/2006 | Budd |
| 7,156,911 B2 | | 1/2007 | Kangas |
| 7,241,437 B2 | | 7/2007 | Davidson |
| 7,649,029 B2 | | 1/2010 | Kolb |
| 7,674,850 B2 | | 3/2010 | Karim |
| 7,700,668 B2 | | 4/2010 | Thalacker |
| 7,816,423 B2 | | 10/2010 | Karim |
| 2003/0152888 A1 | | 8/2003 | Sun |
| 2004/0224283 A1 | | 11/2004 | Sun |
| 2005/0252413 A1 | | 11/2005 | Kangas |
| 2008/0194722 A1 | | 8/2008 | Abuelyaman |
| 2009/0247660 A1 | | 10/2009 | Park |
| 2012/0208965 A1 | | 8/2012 | Joly |
| 2013/0012614 A1 | * | 1/2013 | Abuelyaman et al. ....... 523/115 |

FOREIGN PATENT DOCUMENTS

| | | |
|---|---|---|
| GB | 2347679 | 9/2000 |
| JP | 2008-285645 | 11/2008 |
| WO | WO 01/30305 | 5/2001 |
| WO | WO 01/30307 | 5/2001 |
| WO | WO 03/063804 | 8/2003 |
| WO | WO 2008/082881 | 7/2008 |
| WO | WO 2011/126647 | 10/2011 |
| WO | WO 2012/003136 | 1/2012 |
| WO | WO 2012/112304 | 8/2012 |
| WO | WO 2012/112321 | 8/2012 |

OTHER PUBLICATIONS

Hutson, "Chain Transfer Activity of ω-Unsaturated Methacrylic Oligomers in Polymerizations of Methacrylic Monomers", Macromolecules, Mar. 2004, vol. 37, No. 12, pp. 4441-4452.
International Search Report for PCT International Application No. PCT/US2012/044290, mailed on Jan. 10, 2013, 4 pages.
Matijevic, Surface and Colloid Science, vol. 6, pp. 23-29, (1973).
Moad, "Chain Transfer Activity of ω-Unsaturated Methyl Methacrylate Oligomers" Macromolecules, Sep. 1996, vol. 29, No. 24, pp. 7717-7726.

* cited by examiner

*Primary Examiner* — Walter Webb

(57) ABSTRACT

Presently described are dental compositions comprising one or more fatty mono(meth)acrylates, methods of use, dental articles, and methods of making dental compositions. It has been found that a relatively low concentration of a fatty mono(meth)acrylate can improve the handling characteristics of a dental composition by reducing the tendency of the composition to stick to a dental instrument and/or by reducing the tendency of a dental composition to string when being manipulated by a dental instrument. In one embodiment, a hardenable dental composition is described comprising a polymerizable resin composition comprising at least one multifunctional ethylenically unsaturated monomer; 0.2 to 10 wt-% of one or more fatty mono(meth) acrylate monomers; and at least 50 wt-% of inorganic oxide filler.

12 Claims, 1 Drawing Sheet

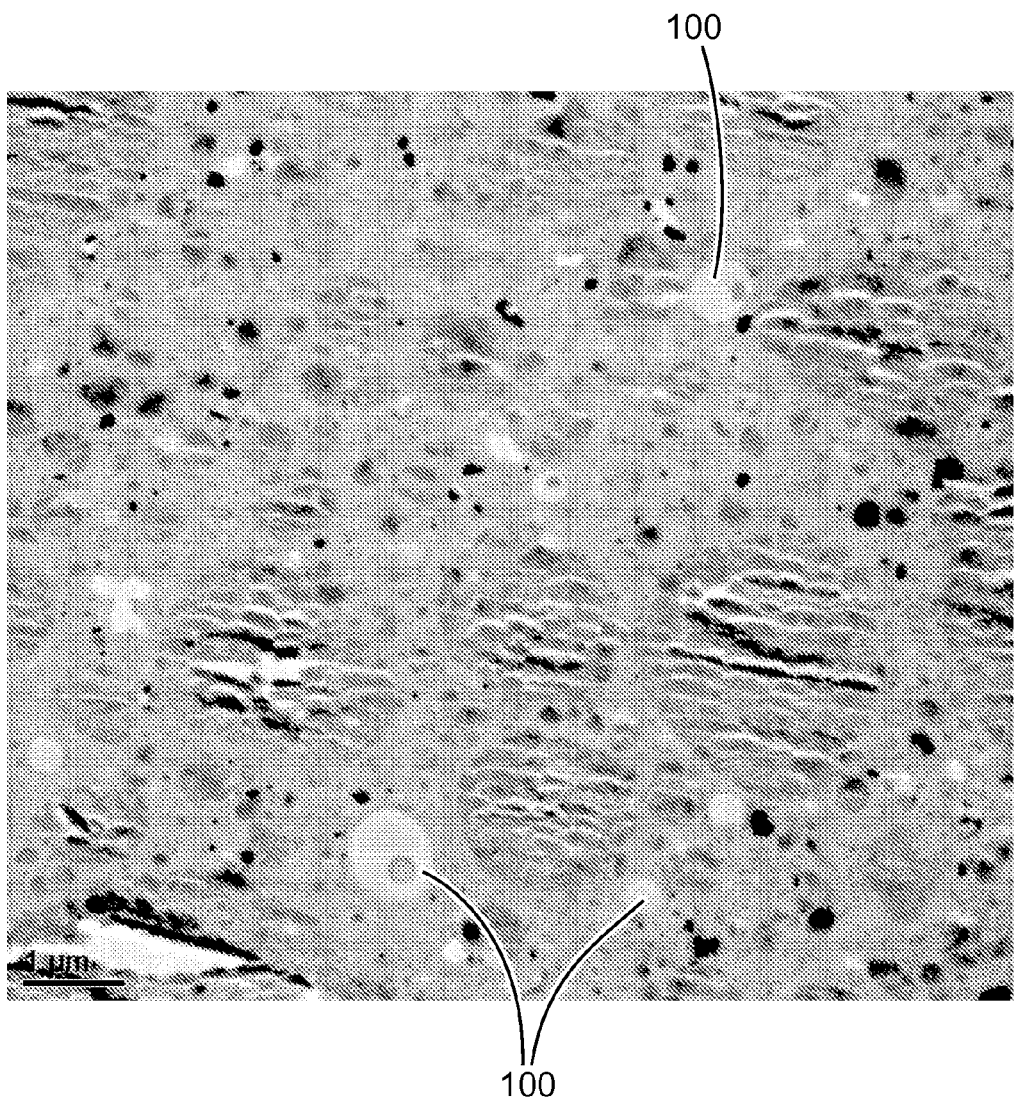

DENTAL COMPOSITIONS COMPRISING A FATTY MONO(METH)ACRYLATE

CROSS REFERENCE TO RELATED APPLICATIONS

This application is a national stage filing under 35 U.S.C. 371 of PCT/US2012/044290, filed Jun. 27, 2012, which claims priority to Provisional Application No. 61/502,500, filed Jun. 29, 2011, the disclosure of which is incorporated by reference in its entirety herein.

SUMMARY

Although various dental compositions have been described, industry would find advantage in (e.g. restoration) materials having improved properties such as improved handling characteristics.

In one embodiment, a method of making a dental composition is described. The method comprises providing a hardenable dental composition wherein the dental composition exhibits tackiness or stringiness when manipulated with a dental instrument; and adding a sufficient amount of one or more fatty mono(meth)acrylate monomer such that the tackiness or stringiness is substantially reduced. In some embodiments, the fatty mono(meth)acrylate monomer comprises an alkyl group having greater than 12 carbon atoms. In this embodiment, the fatty mono(meth)acrylate monomer can be present in the polymerizable resin composition in an amount up to 15 wt-%. In other embodiments, the fatty mono(meth)acrylate monomer comprises an alkyl group having 6 to 12 carbon atoms. In this embodiment, the fatty mono(meth)acrylate monomer is present in the polymerizable resin composition in an amount up to 20 wt-%.

In one favored embodiment, the hardenable dental composition is a dental restoration material comprising an appreciable amount (e.g. at least 50 wt-%) of inorganic oxide filler. In this embodiment, the hardenable dental composition typically comprises 0.2 to 10 wt-% of a fatty mono(meth)acrylate monomer(s). Such hardenable dental composition typically comprises at least one multifunctional ethylenically unsaturated monomer.

In another embodiment, a method of treating a tooth surface is described. The method comprises providing a hardenable dental composition comprising one or more fatty mono(meth)acrylate monomers as described herein; placing the hardenable dental composition on a tooth surface; and hardening the hardenable dental composition.

Dental restoration materials can be utilized to form a dental article (e.g. such as a crown). Thus, in another embodiment dental articles are described comprising the hardenable dental composition, as described herein, at least partially hardened.

Each of these embodiments may further be characterized by any one or combination of various features, as described herein. The hardenable dental composition is typically sufficiently flowable such that the composition can be extruded through an orifice with a force no greater than 20 kg for an orifice diameter of 2 mm. The fatty mono(meth)acrylate monomer phase separates from the polymerizable resin composition such that the fatty mono(meth)acrylate forms microscopic domains. Such phase separation may increase the contrast ratio of the hardenable dental composition by at least 5. In some embodiments, the composition has a contrast ratio of at least 45, yet can be free of opacifying pigment. In some embodiments, the composition has a ratio of contrast ratio to depth of cure of at least 10.

BRIEF DESCRIPTION OF THE DRAWING

FIG. 1 is a transmission electron microscopy image of a cross-section of an embodied cured dental composition.

DETAILED DESCRIPTION

As used herein, "dental composition" refers to a material, optionally comprising filler, capable of adhering or being bonded to an oral surface.

"Hardenable" and "curable' are descriptive of a material or composition that can be cured (e.g., polymerized or crosslinked) by heating to induce polymerization and/or crosslinking; irradiating with actinic irradiation to induce polymerization and/or crosslinking; and/or by mixing one or more components to induce polymerization and/or crosslinking. "Mixing" can be performed, for example, by combining two or more parts and mixing to form a homogeneous composition. Alternatively, two or more parts can be provided as separate layers that intermix (e.g., spontaneously or upon application of shear stress) at the interface to initiate polymerization.

A curable dental composition can be used to bond a dental article to a tooth structure, be used as a restorative that is placed directly into the mouth and cured in-situ, or alternatively be used to fabricate a prosthesis outside the mouth that is subsequently adhered within the mouth.

Curable dental compositions include, for example, adhesives (e.g., dental and/or orthodontic adhesives), cements (e.g., resin-modified glass ionomer cements, and/or orthodontic cements), liners (applied to the base of a cavity to reduce tooth sensitivity), and resin restoratives (also referred to as direct composites) such as dental fillings, as well as crowns, bridges, and articles for dental implants. Highly filled dental compositions are also used for mill blanks, from which a crown may be milled. A composite or dental restoration material is a highly filled paste designed to be suitable for filling substantial defects in tooth structure. Dental cements are somewhat less filled and less viscous materials than composites, and typically act as a bonding agent for additional materials, such as inlays, onlays and the like, or act as the filling material itself if applied and cured in layers. Dental cements are also used for permanently bonding dental restorations such as a crown or bridge to a tooth surface or an implant abutment.

"Hardened" refers to a material or composition that has been cured (e.g., polymerized or crosslinked).

"Hardener" refers to something that initiates hardening of a resin. A hardener may include, for example, a polymerization initiator system, a photoinitiator system, a thermal initiator and/or a redox initiator system.

"Shrinkage" refers to the volumetric change as a result of curing, i.e. shrinkage that occurs after gelation as can be measured using the Watts Shrinkage (Watts) test method as described in WO2011/126647. Hence, shrinkage does not refer to the volumetric change that occurs prior to gelation. "Dental article" refers to an article that can be adhered (e.g., bonded) to a tooth structure or dental implant. Dental articles include, for example, crowns, bridges, veneers, inlays, onlays, fillings, orthodontic appliances and devices.

"Orthodontic appliance" refers to any device intended to be bonded to a tooth structure, including, but not limited to, orthodontic brackets, buccal tubes, lingual retainers, orthodontic bands, bite openers, buttons, and cleats. The appliance has a base for receiving adhesive and it can be a flange made of metal, plastic, ceramic, or combinations thereof. Alternatively, the base can be a custom base formed from cured adhesive layer(s) (i.e. single or multi-layer adhesives).

"Oral surface" refers to a soft or hard surface in the oral environment. Hard surfaces typically include tooth structure including, for example, natural and artificial tooth surfaces, bone, and the like.

"(Meth)acrylate" is a shorthand reference to acrylate, methacrylate, or combinations thereof; "(meth)acrylic" is a shorthand reference to acrylic, methacrylic, or combinations thereof; and "(meth)acryl" is a shorthand reference to acryl, methacryl, or combinations thereof.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

Presently described are dental compositions comprising one or more fatty mono(meth)acrylates, methods of use, dental articles, and methods of making dental compositions.

It has been found that a relatively low concentration of a fatty mono(meth)acrylate can improve the handling characteristics of a dental composition by reducing the tendency of the composition to stick to a dental instrument and/or by reducing the tendency of a dental composition to string when being manipulated by a dental instrument.

Without intending to be bound by theory, it is surmised that the fatty mono(meth)acrylate(s) phase separates during use. Evidence of such phase separation can be detected using transmission microscopy. With reference to FIG. 1, a transmission electron microscopy image of a cross-section of an embodied cured dental composition, the fatty mono(meth) acrylate phase separates to form microscopic domains 100, on the order of magnitude of about 0.5 to 1 micron. Hence, such phase separation is typically not a "bulk" phase separation as would result in the fatty mono(meth)acrylate forming a separate layer that can be redispersed in the polymerizable resin composition. Such phase separation is amenable to increasing the opacity or contrast ratio, with or without opacifying pigments. In some embodiments, the addition of the fatty mono(meth)acrylate(s) to an (e.g. unpigmented) polymerizable resin of the hardenable dental composition increases the contrast ratio by at least 5, or 10, or 15, or 20.

By increasing the opacity or contrast ratio, the concentration of opacifying pigments can be reduced. In some embodiments, the hardenable dental composition may be free of opacifying pigments. Reducing the concentration of pigments can improve the depth of cure. In some embodiments, the (e.g. filled) dental compositions described herein exhibit a ratio of contrast ratio to depth of cure of at least 10, 11, 12, 13, 14, or 15. This ratio is typically no greater than 25 or 20.

The fatty mono(meth)acrylate comprises a straight chain or branched alkyl group having greater than 5 carbon atoms. The alkyl group may optionally comprise substituents provided that the substituted alkyl group remains substantially hydrophobic.

In some embodiments, the fatty mono(meth)acrylate monomer comprises an alkyl group having at least 6, or 7, or 8 carbon atoms and no greater than 12 carbon atoms. In this embodiment, the fatty mono(meth)acrylate monomer is present in the polymerizable resin composition in an amount up to 20 or 25 wt-%. In other embodiments, the fatty mono(meth)acrylate monomer comprises an alkyl group having greater than 12 carbon atoms. In this embodiment, the fatty mono(meth)acrylate monomer can be present in the polymerizable resin composition in an amount up to 15 wt-%. The chain length of the alkyl group (i.e. R) is typically no greater than 50 carbons atoms or 40 carbons. As the chain length of the alkyl group increase, the melt point tends to also increase. In some embodiments, the chain length of the alkyl group is no greater than 35, or 30, or 25 carbon atoms.

Various fatty mono(meth)acrylates are commercially available. Fatty mono(meth)acrylates can be formed by reacting the hydroxyl group of a fatty alcohol or derivative thereof with a (meth)acrylic acid, a (meth)acryloyl halide, or a hydroxyl-reactive (meth)acrylate compound. Various fatty alcohols are known including dodecyl alcohol, cetyl alcohol $CH_3(CH_2)_{15}OH$, stearyl alcohol (also known as octadecyl alcohol or 1-octadecanol), and oleyl alcohol.

Without intending to be bound by theory, it is surmised that the chain length of the alkyl group (i.e. R) may relate to the rate of phase separation. For example, fatty mono(meth) acrylates comprising longer chain alkyl groups may phase separate faster than fatty mono(meth)acrylates comprising shorter alkyl groups.

The fatty mono(meth)acrylate preferably has a melt point no greater than about 30° C. In some embodiments, the fatty mono(meth)acrylate is a liquid at 25° C. One favored fatty mono(meth)acrylate is stearyl methacrylate, having a melt point of 23° C.

The hardenable dental composition is preferably a dental restoration material comprising an appreciable amount of inorganic oxide filler. The concentration of fatty mono (meth)acrylate(s) in the filled polymerizable resin composition is typically at least 0.2, or 0.3, or 0.4, or 0.5 wt-% and generally no greater than 15 wt-%, 14 wt-%, 13 wt-%, 12 wt-%, 11 wt-%, or 10 wt-%. In some embodiments, the concentration of fatty mono(meth)acrylate(s) in the filled polymerizable resin composition is no greater, than 9 wt-% or 8 wt-% or 7 wt-% or 6 wt-% or 5 wt-%. A concentration of about 1 wt-% to about 5 wt-% can be preferred for embodiments wherein the that fatty mono(meth)acrylate is stearyl methacrylate. However, when the chain length is greater than 18 carbon atoms, a lower concentration may be suitable. Further, when the chain length is less than 18 carbon atoms, higher concentrations may be needed to obtain the desired result. As the concentration of fatty mono(meth)acrylate increases, the mechanical properties, such as Diametral Tensile Strength, can decrease. Hence, in some embodiments, it is preferred to utilize the minimum concentration that will provide improved handling properties (e.g. sufficient reduction in tack and/or stringing). However, as the concentration of fatty mono(meth)acrylate increases, the contrast ratio typically also increases. When this technical effect is desired it may be preferred to utilize a higher concentration than the "minimal" concentration provided that the Diametral Tensile Strength is at least 50 MPa, 55 MPa or 60 MPa.

The fatty mono(meth)acrylate is typically present as phase separated microscopic domains, as previously described. For embodiments wherein the fatty mono(meth)acrylate has a melt point above ambient temperature 20-25° C., the fatty mono(meth)acrylate is present as solid domains within a flowable liquid polymerizable resin composition. In the absence of heat or pressure, a flowable liquid generally forms to the shape of its container within minutes or hours. Hence, a mixture of the fatty mono(meth)acrylate dispersed within the polymerizable resin composition is not a solid, or semi-solid having a wax-like consistency.

Regardless of the melt point, the fatty mono(meth)acrylate(s) is generally initially dissolved or dispersed in the unfilled or filled polymerizable resin composition. For embodiments wherein the fatty mono(meth)acrylate has a melt point above room temperature, the (e.g. unfilled or filled) polymerizable resin composition is typically sufficiently heated such that the fatty (mono)methacrylate is a liquid, rather than a solid. Heating can also reduce the viscosity of other the other polymerizable components of the polymerizable resin, which in turn can also aid in dispersing the fatty mono(meth)acrylate.

In some embodiments, the filled hardenable dental composition is also sufficiently flowable such that it can be dispensed from a narrow-tip syringe, typically 20 gauge or similar, under hand pressure. In other embodiments, the hardenable dental composition can be extruded through an orifice with a force no greater than 20 kg for an orifice diameter of 2 mm. In some embodiments, the extrusion force is no greater than 15, or 14, or 13, or 12, or 11, or 10 kg. The extrusion force is typically at least 1 or 2 kg and in some embodiments, at least 3, 4, or 5 kg.

The hardenable (e.g. dental) compositions described herein further comprise at least one ethylenically unsaturated monomer or oligomer in combination with the fatty mono(meth)acrylate. In some embodiments, such as dental restorations the ethylenically unsaturated monomer is multifunctional. The phrase "multifunctional ethylenically unsaturated" means that the monomers each comprise at least two ethylenically unsaturated (e.g. free radically) polymerizable groups, such as (meth)acrylate groups.

In favored embodiments, such ethylenically unsaturated group is a (e.g. terminal) free radically polymerizable group including (meth)acryl such as (meth)acrylamide ($H_2C=CHCON-$ and $H_2C=CH(CH_3)CON-$) and (meth)acrylate ($CH_2CHCOO-$ and $CH_2C(CH_3)COO-$). Other ethylenically unsaturated polymerizable groups include vinyl ($H_2C=C-$) including vinyl ethers ($H_2C=CHOCH-$). The ethylenically unsaturated terminal polymerizable group(s) is preferably a (meth)acrylate group, particularly for compositions that are hardened by exposure to actinic (e.g. UV) radiation. Further, methacrylate functionality is typically preferred over the acrylate functionality in curable dental compositions.

The ethylenically unsaturated monomer may comprise various ethylenically unsaturated monomers, as known in the art, for use in dental compositions.

In some favored embodiments, the (e.g. dental) composition comprises one or more ethylenically unsaturated (e.g. (meth)acrylate) monomers having a low volume shrinkage monomer. Preferred (e.g. filled) dental compositions (useful for restorations such as fillings and crowns) described herein comprise one or more low volume shrinkage monomers such that the composition exhibits a Watts Shrinkage of less than about 2%. In some embodiments, the Watts Shrinkage is no greater than 1.90%, or no greater than 1.80%, or no greater than 1.70%, or no greater than 1.60%. In favored embodiments, the Watts Shrinkage is no greater than 1.50%, or no greater than 1.40%, or no greater than 1.30%, and in some embodiments no greater than 1.25%, or no greater than 1.20%, or no greater than 1.15%, or no greater than 1.10%.

Preferred low volume shrinkage monomers include isocyanurate monomers, such as described in WO2011/126647; polymerizable monomers described in WO2012/003136; polymerizable compounds having at least one cyclic allylic sulfide moiety such as described in US2008/0194722; methylene dithiepane silanes as described in U.S. Pat. No. 6,794,520; oxetane silanes such as described in U.S. Pat. No. 6,284,898; and di-, tri, and/or tetr-(meth)acryloyl-containing materials such as described in WO2008/082881; each of which are incorporated herein by reference.

It has been found that polymerizable resin composition comprising low volume shrinkage monomers such as isocyanurate monomers and/or ethoxylated resorcinol monomers exhibit the desired phase separation when combined with a fatty mono(meth)acrylate(s), as described herein.

In some embodiments, the majority of the (e.g. unfilled) polymerizable resin composition comprises one or more low volume shrinkage monomers. For example, at least 50%, 60%, 70%, 80%, 90% or more of the (e.g. unfilled) polymerizable resin may comprise low volume shrinkage monomer(s).

In one embodiment, the dental composition comprises at least one isocyanurate monomer. The isocyanurate monomer generally comprises a trivalent isocyanuric acid ring as an isocyanurate core structure and at least two ethylenically unsaturated (e.g. free radically) polymerizable groups bonded to at least two of the nitrogen atoms of the isocyanurate core structure via a (e.g. divalent) linking group. The linking group is the entire chain of atoms between the nitrogen atom of the isocyanurate core structure and the terminal ethylenically unsaturated group. The ethylenically unsaturated (e.g. free radically) polymerizable groups are generally bonded to the core or backbone unit via a (e.g. divalent) linking group.

The trivalent isocyanurate core structure generally has the formula:

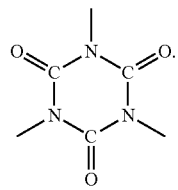

The divalent linking group comprises at least one nitrogen, oxygen or sulfur atom. Such nitrogen, oxygen or sulfur atom forms an urethane, ester, thioester, ether, or thioether linkage. Ether and especially ester linkages can be beneficial over isocyanurate monomers comprising urethane linkages for providing improved properties such as reduced shrinkage, and/or increased mechanical properties, e.g., diametral tensile strength (DTS). Thus, in some embodiments, the divalent linking groups of the iscosyanurate monomer are free of urethane linkages. In some favored embodiments, the divalent linking group comprises an ester linkage such as an aliphatic or aromatic diester linkage.

The isocyanurate monomer typically has the general structure

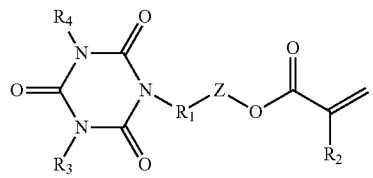

wherein $R_1$ is a straight chain, branched or cyclic alkylene, arylene, or alkarylene, optionally including a heteroatom (e.g. oxygen, nitrogen, or sulfur); $R_2$ is hydrogen or methyl; Z is alkylene, arylene, or alkarylene linking group comprising at least one moiety selected from urethane, ester, thioester, ether, or thioether, and combinations of such moieties; and at least one of $R_3$ or $R_4$ is

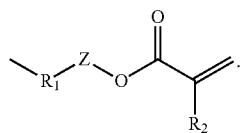

$R_1$ is typically a straight chain, branched or cyclic alkylene, optionally including a heteroatom, having no greater than 12 carbons atoms. In some favored embodiments, $R_1$ has no greater than 8, 6, or 4 carbon atoms. In some favored embodiments, $R_1$ comprises at least one hydroxyl moiety.

In some embodiments, Z comprises an aliphatic or aromatic ester linkage such as a diester linkage.

In some embodiment, Z further comprises one or more ether moieties. Hence, the linking group may comprise a combination of ester or diester moieties and one or more ether moieties.

For embodiments, wherein the isocyanurate monomer is a di(meth)acrylate monomer, $R_3$ or $R_4$ is hydrogen, alkyl, aryl, or alkaryl, optionally including a heteroatom.

$R_1$ is generally derived from the starting (e.g. hydroxy terminated) isocyanurate precursor. Various isocyanurate precursor materials are commercially available from TCI America, Portland, Oreg. The structures of exemplary isocyanurate precursor materials are depicted as follows:

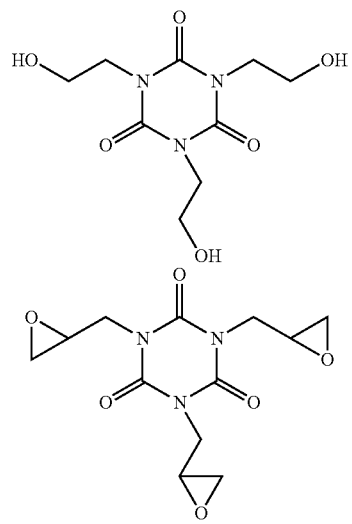

The isocyanurate (meth)acrylate monomers disclosed herein having a linking groups comprising an oxygen atom of an ester moiety were generally prepared by reaction of hydroxy or epoxy terminated isocyanurates with (meth)acrylated carboxylic acids such as mono-(2-methacryloxyethyl)phthalic acid and mono-(2-methacryloxytheyl)succinic acid.

Suitable (meth)acrylated carboxylic acids include for example mono-(2-methacryloxyethyl)phthalic acid(s), mono-(2-methacryloxytheyl)succinic acid, and mono-(2-methacryloxyethyl)maleic acid. Alternatively, the carboxylic acid may comprise (meth)acrylamido functionally such as methacrylamido derivatives of naturally occurring amino acids such as methacrylamidoglycine, methacrylamidoleucine, methacrylamidoalanine etc.

In some embodiments, a single(meth)acrylated carboxylic acid is reacted with a single hydroxyl terminated isocyanurate (e.g. tris-(2-hydroxylethyl)isocyanurate). When a sufficient molar ratio of (meth)acrylate carboxylic acid is utilized such that all the hydroxyl groups of the ring are reacted, such synthesis can produce a single reaction product wherein each of the free radically terminated groups, bonded to the nitrogen atoms of the trivalent isocyanuric acid ring, are the same. However, when a single epoxy terminated isocyanurate is reacted with a single carboxylic acid, the reaction product generally comprises more than one isomer in the reaction product.

When two different hydroxy or epoxy terminated isocyanurates and/or two different (e.g. (meth)acrylated) carboxylic acids are utilized, a statistical mixture of reaction products are obtained based on the relative amounts of reactants. For example, when a mixture of a (meth)acrylated aromatic carboxylic acid and a (meth)acrylate aliphatic carboxylic acid are utilized, some of the free radically terminated divalent linking groups bonded to the nitrogen atom of the trivalent isocyanuric acid ring comprise an aromatic group, whereas others do not. Further, when a combination (e.g. 1 equivalent) of a hydroxyl terminated carboxylic acid and (e.g. 2 equivalents) of a monocarboxylic acid (such as octanoic acid) is reacted with a single hydroxyl terminated isocyanurate (e.g. tris-(2-hydroxylethyl)isocyanurate), a mono(meth)acrylate isocyanurate can be prepared as further described in WO2011/126647. Such mono(meth)acrylate isocyanurate is suitable for use as a reactive diluent.

Alternatively, isocyanurate (meth)acrylate monomers having ether group containing linking groups can be synthesized. For example, in one illustrative synthesis, phthalic acid anhydride can be reacted with a mono-methacrylated di, tri, tetra or polyethylenegylcol in the presence of a catalytic amount of 4-(dimethylamino)pyridine (DMAP) and butylated hydroxytoluene inhibitor (BHT) at 95° C. for a 3-6 hours to form a mono-methaycrylated polyethyleneglycol phthalic acid mono-ester. The obtained methacrylated acid can be reacted, in acetone, with tris-(2-hydroxyethyl)isocyanurate using dicyclohexyl carbodiimide (DCC) at 0-5° C. then at room temperature. Such reaction scheme is depicted as follows:

In another illustrative synthesis, tris(2-hydroxyethyl)isocyanurate can be reacted with ethylene oxide to form a polyethylene glycol terminated with a hydroxyl group. The OH termini can be esterified with meth(acrylic) acid to provide a product where the linking group is a polyether. Such reaction scheme is depicted as follows:

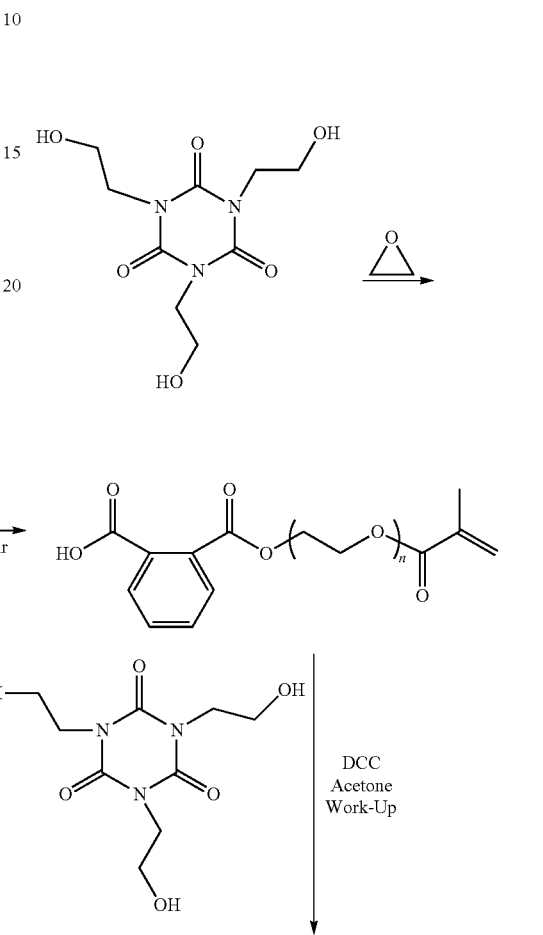

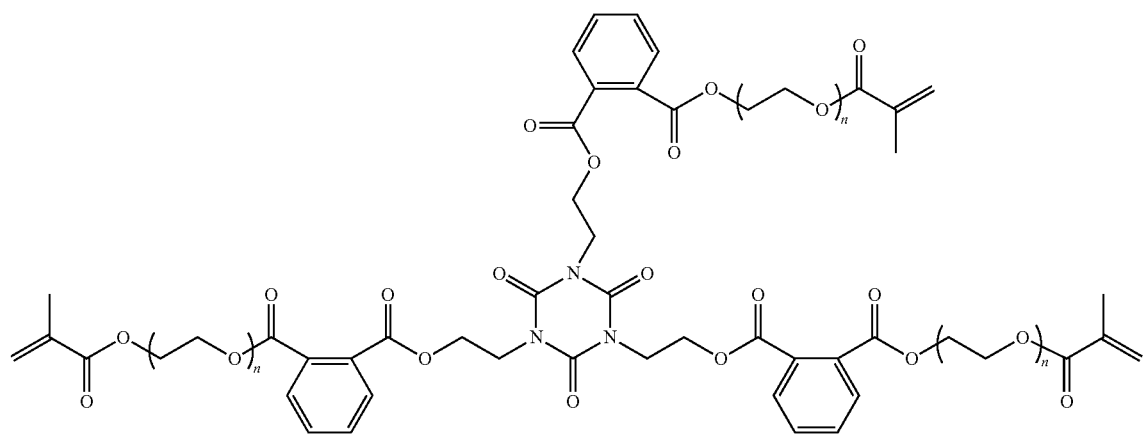

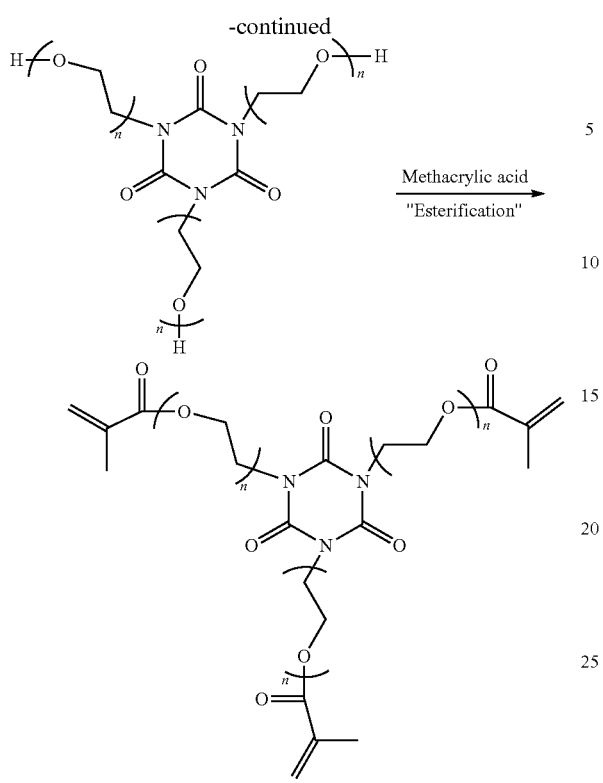

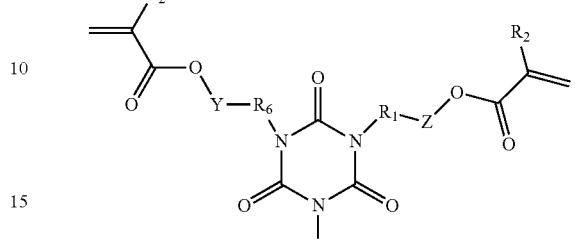

The isocyanurate monomer is preferably a multi(meth)acrylate such as a di(meth)acrylate isocyanurate monomer or a tri(meth)acrylate isocyanurate monomer.

The di(meth)acrylate monomer has the general structure:

wherein $R_1$, $R_2$, $R_3$ and Z are as previously described; $R_6$ is a straight chain, branched, or cyclic alkylene, arylene, or alkarylene, optionally including a heteroatom (e.g. oxygen, nitrogen, or sulfur); and Y is alkylene, arylene, or alkarylene linking group comprising at least one moiety selected from urethane, ester, thioester, ether, or thioether, and combinations of such moieties.

Illustrative di(meth)acrylate isocyanurate monomers includes:

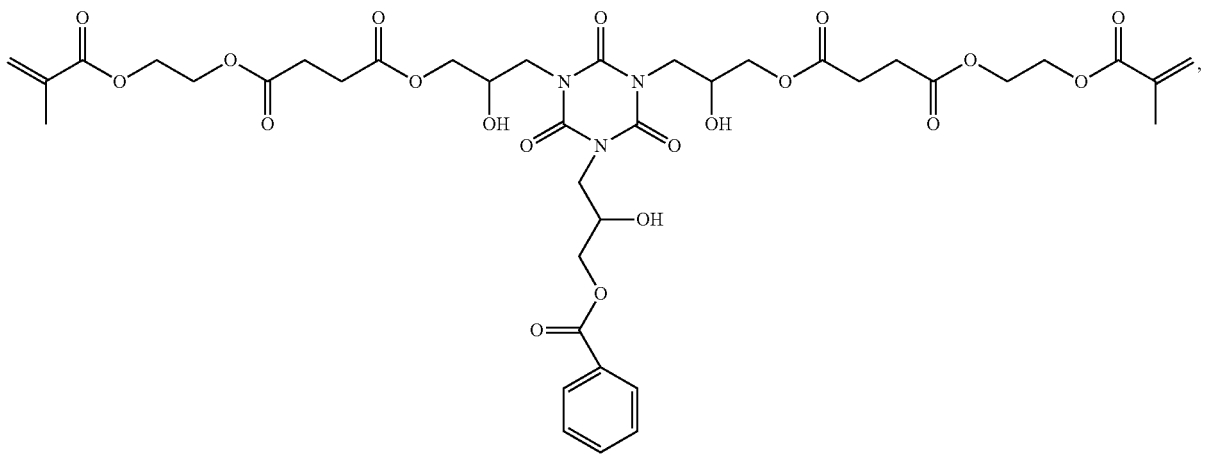

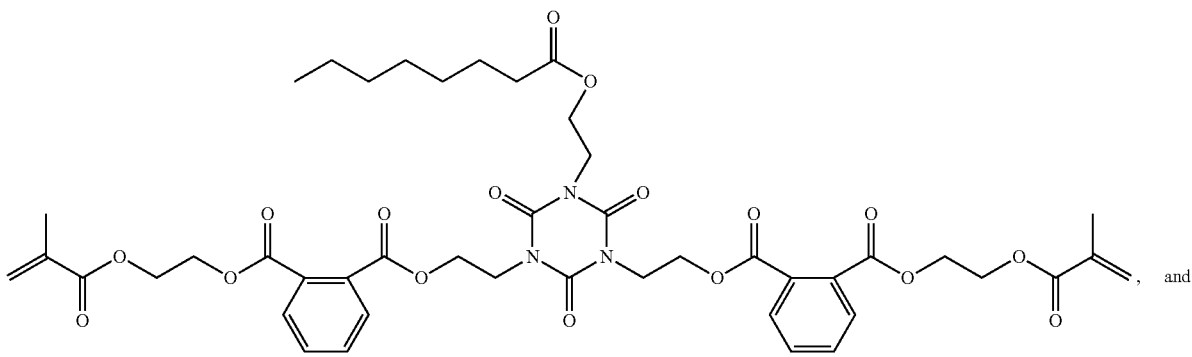

-continued

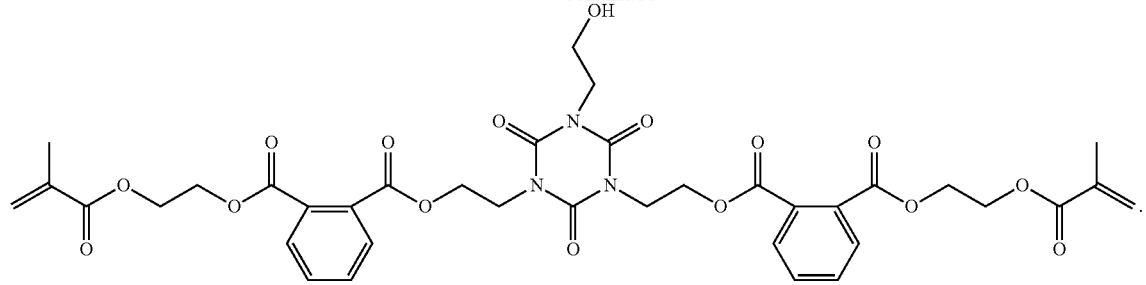

In some favored embodiments, the tri(meth)acrylate monomer has the general structure:

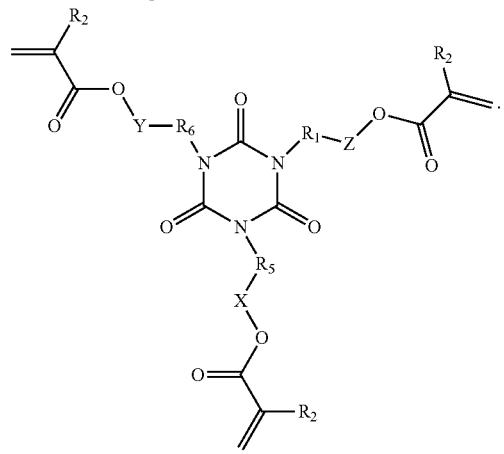

wherein $R_1$, $R_5$, and $R_6$ are independently a straight chain, branched, or cyclic alkylene, arylene, or alkarylene, optionally including a heteroatom (e.g. oxygen, nitrogen, or sulfur); $R_2$ is hydrogen or methyl; X, Y, and Z are independently alkylene, arylene, or alkarylene linking group comprising at least one moiety selected from urethane, ester, thioester, ether, thioether, or combinations of such moieties; and $R_2$ is hydrogen or methyl.

In some embodiments, $R_1$, $R_5$, and $R_6$ comprise at least one hydroxyl moiety.

Illustrative tri(meth)acrylate isocyanurate monomers include for example:

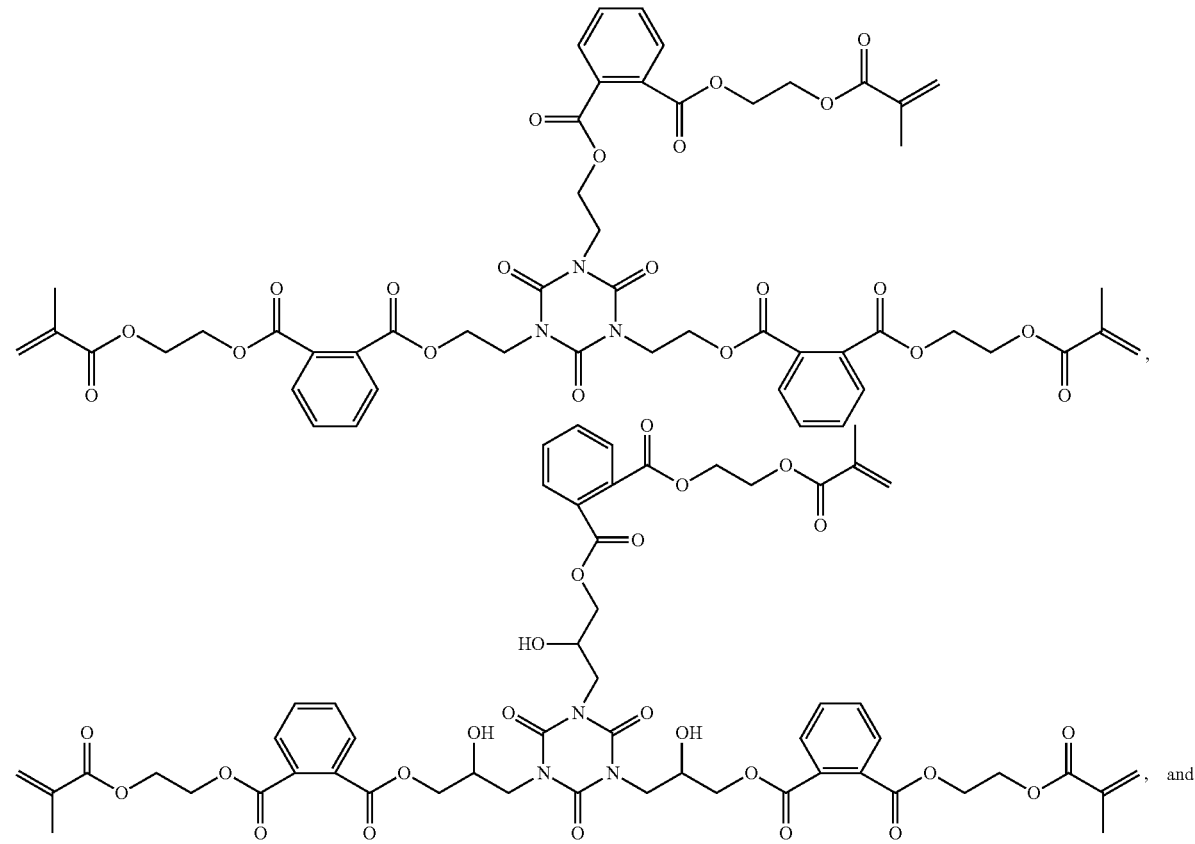

and

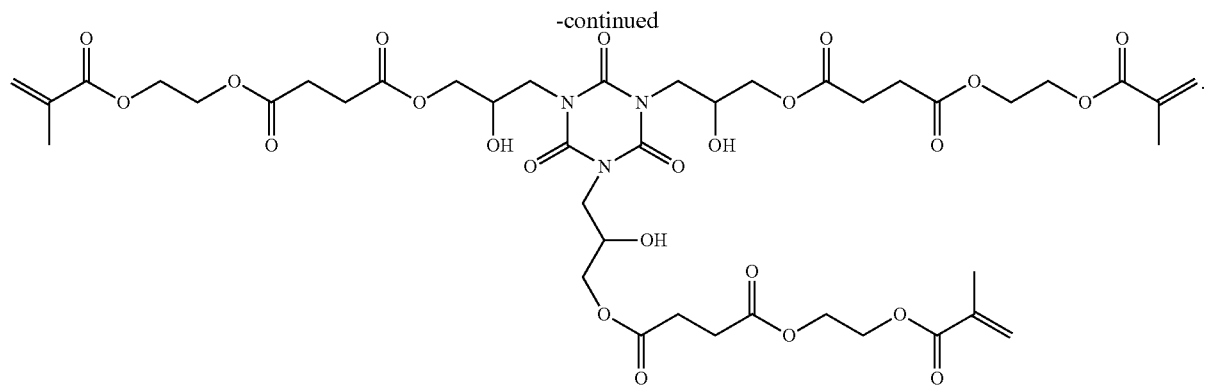

The polymerizable resin portion of the hardenable unfilled dental composition described herein may comprise at least 10 wt-%, 15 wt-%, 20 wt-%, or 25 wt-%, multifunctional ethylenically unsaturated isocyanurate monomer(s). The isocyanurate monomer may comprise a single monomer or a blend of two or more isocyanurate monomers. The total amount of isocyanurate monomer(s) in the unfilled polymerizable resin portion of the hardenable (i.e. polymerizable) dental composition is typically no greater than 90 wt-%, 85 wt-%, 80 wt-%, or 75 wt-%.

The filled hardenable dental composition described herein typically comprises at least 5 wt-%, 6 wt-%, 7 wt-%, or 8 wt-% of multifunctional ethylenically unsaturated isocyanurate monomer(s). The total amount of isocyanurate monomer(s) of the filled hardenable (i.e. polymerizable) dental composition is typically no greater than 20 wt-%, or 19 wt-%, or 18 wt-%, or 17 wt-%, or 16 wt-%, or 15 wt-%.

In some embodiments, the composition comprises a multifunctional ethylenically unsaturated isocyanurate monomer and a low volume shrinkage monomer as described in previously cited WO2012/003136, such as a multifunctional ethylenically unsaturated ethoxylated resorcinol (ER) monomer. Ethoxylated resorcinol (ER) monomers generally have the core structure (i.e. backbone unit (U):

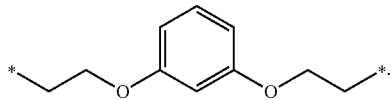

Such ethoxylated resorcinol (ER) monomers can be prepared for example from starting materials such as The backbone unit (U) typically comprises one or two spacer unit(s) (S) bonded to the backbone unit via an ether linkage. In some embodiments, the speacer unit(s) S typically comprises

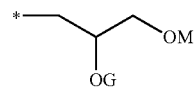

wherein M=acroyl, methacroyl or phenyl.
"G" may comprise a moiety selected from

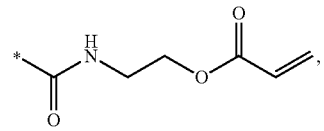

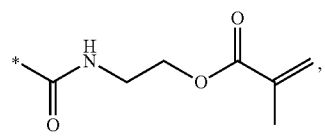

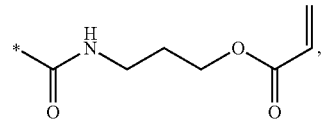

| ER | 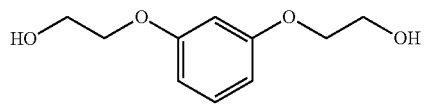 |
|---|---|
| | Ethoxylated resorcinol (CAS no. 102-40-9) |
| ERGP | 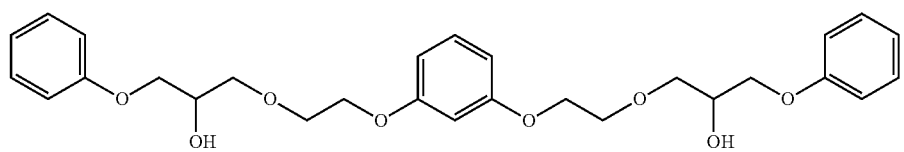 |
| | Mw = 498.6 |

17
-continued
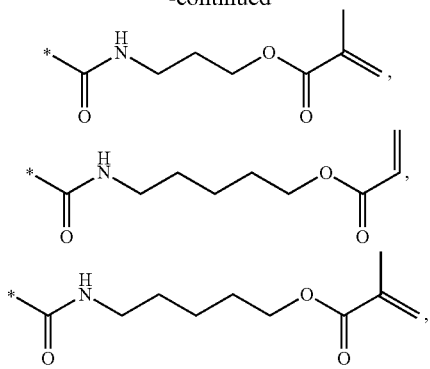
18
-continued
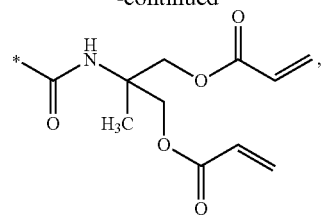
as well as combinations and mixtures of such "G" moieties.
Some illustrative species of such multifunctional ethylenically unsaturated ethoxylated resorcinol (ER) monomers are described in the following table:
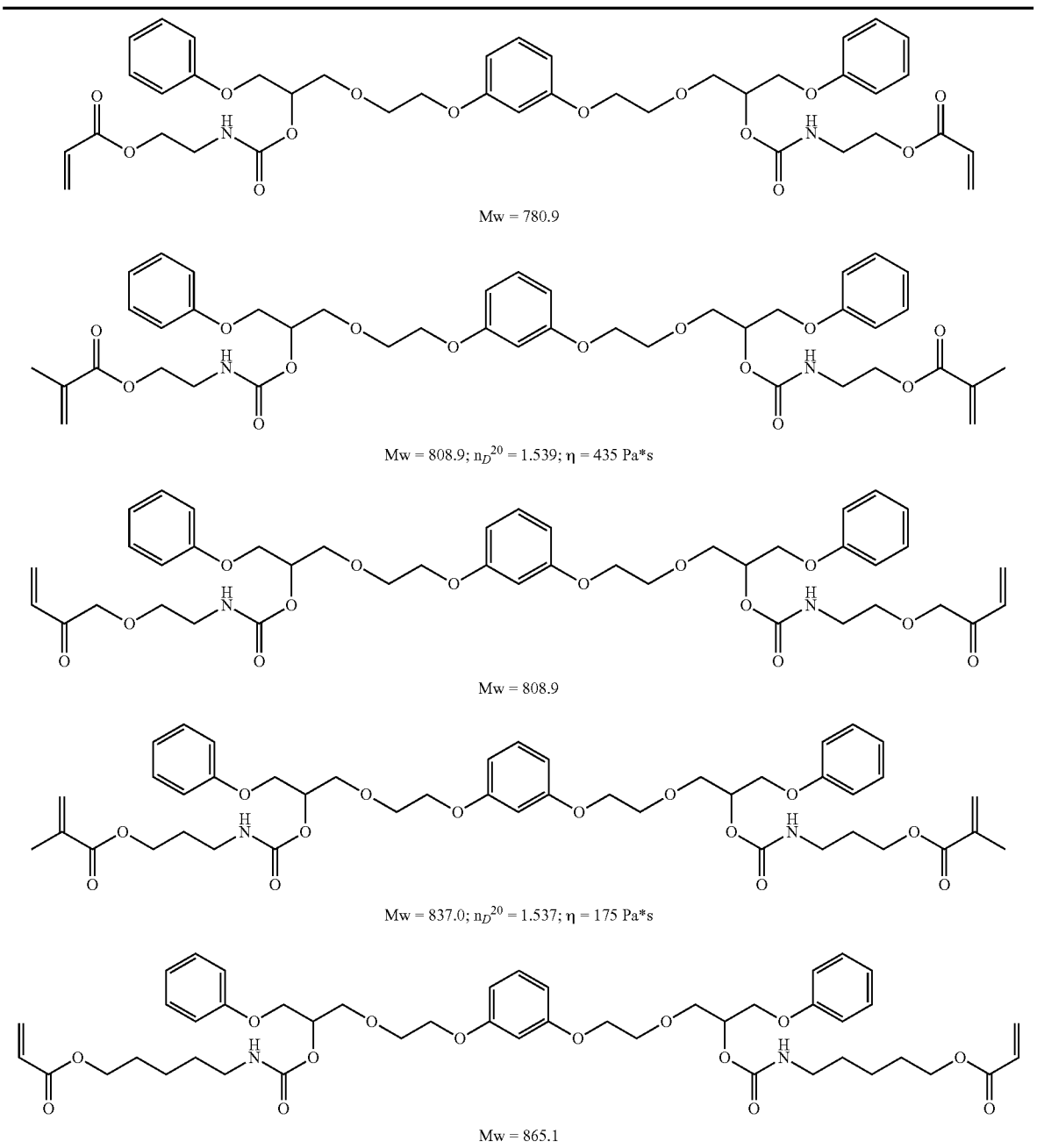
Mw = 780.9
Mw = 808.9; $n_D^{20}$ = 1.539; $\eta$ = 435 Pa*s
Mw = 808.9
Mw = 837.0; $n_D^{20}$ = 1.537; $\eta$ = 175 Pa*s
Mw = 865.1

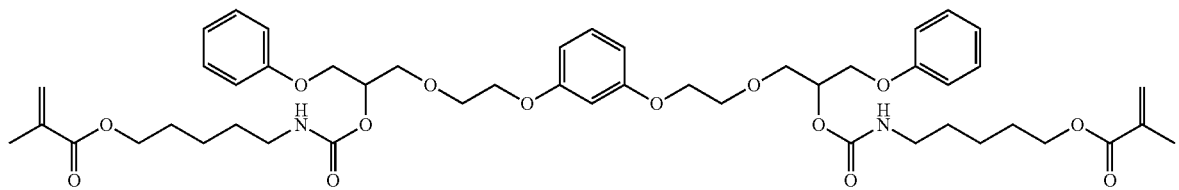
Mw = 893.1; $n_D^{20}$ = 1.535; η = 45 Pa*s
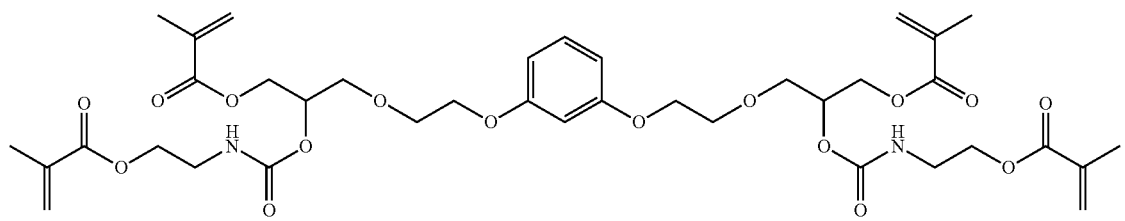
Mw = 792.8
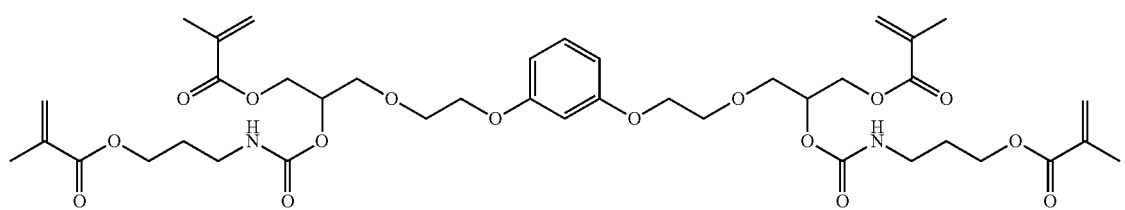
Mw = 820.9
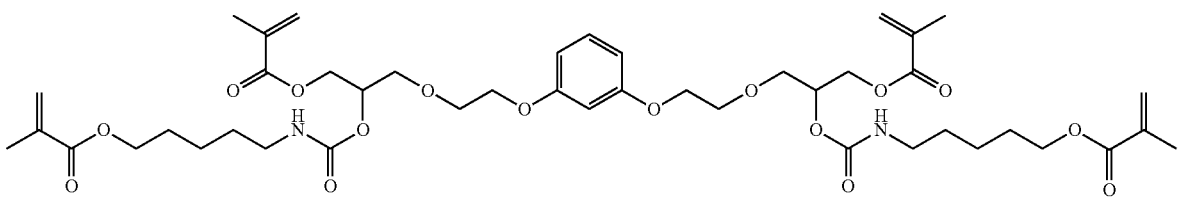
Mw = 877.0
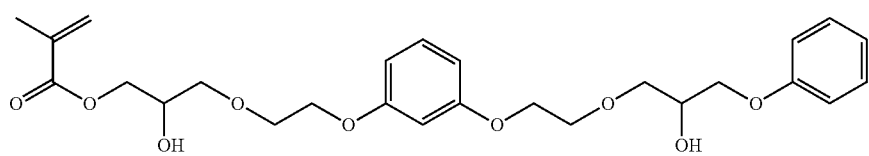
Mw = 490.6
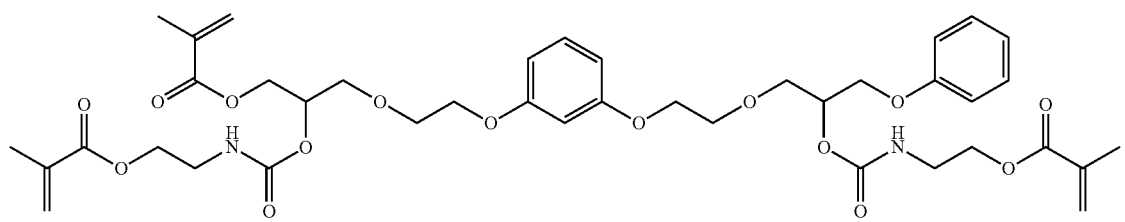
Mw = 800.9

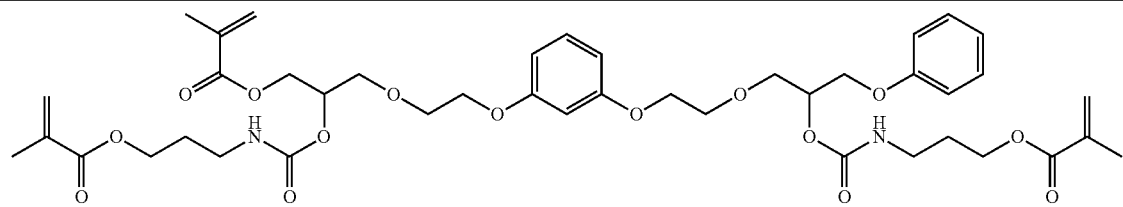

Mw = 829.0

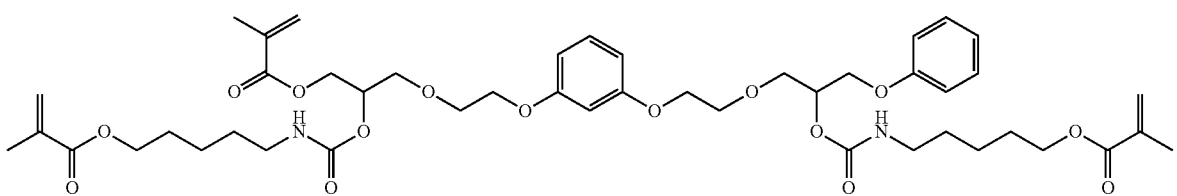

Mw = 885.1

In some embodiments, the (i.e. calculated) molecular weight of the low shrink (e.g. isocyanurate and ethoxylated resorcinol) monomers is typically no greater than 2000 g/mole. In some embodiments, the molecular weight of the monomers is no greater than about 1500 g/mole or 1200 g/mole or 1000 g/mole. The molecular weight of the monomers is typically at least 600 g/mole.

The ethylenically unsaturated monomers of the dental composition are typically stable liquids at about 25° C. meaning that the monomer do not substantially polymerize, crystallize, or otherwise solidify when stored at room temperature (about 25° C.) for a typical shelf life of at least 30, 60, or 90 days. The viscosity of the monomers typically does not change (e.g. increase) by more than 10% of the initial viscosity.

Particularly for dental restoration compositions, the ethylenically unsaturated monomers generally have a refractive index of at least 1.50. In some embodiments, the refractive index is at least 1.51, 1.52, 1.53, or greater. The inclusion of sulfur atoms and/or the present of one or more aromatic moieties can raise the refractive index (relative to the same molecular weight monomer lacking such substituents).

In some embodiments, the (unfilled) polymerizable resin may comprise solely one or more low shrink monomers in combination with the one or more fatty mono(meth)acrylate(s). In other embodiments, the (unfilled) polymerizable resin further comprises (e.g. a small concentration of) other monomer(s). By "other" is it meant an ethylenically unsaturated monomer such as a (meth)acrylate monomer that is not a low volume shrinkage monomer.

The concentration of such other monomer(s) is typically no greater than 20 wt-%, 19 wt-%, 18 wt-%, 17 wt-%, 16 wt-%, or 15 wt-% of the (unfilled) polymerizable resin portion. The concentration of such other monomers is typically no greater than 5 wt-%, 4 wt-%, 3 wt-%, or 2 wt-% of the filled polymerizable dental composition.

In some embodiments, the dental composition comprises a low viscosity reactive (i.e. polymerizable) diluent. Reactive diluents are typically relatively low in molecular weight, having a molecular weight less than 600 g/mole, or 550 g/mol, or 500 g/mole. Reactive diluents typically comprise one or two ethylenically unsaturated groups such as in the case of mono(meth)acrylate or di(meth)acrylate monomers. In some embodiments, the filled dental composition comprises 0.5 to about 5 wt-% of reactive diluents. One suitable low viscosity reactive diluent is dodecanediol dimethacrylate (DDMA).

The hardenable dental composition may further comprise an addition fragmentation agent. The addition-fragmentation agent may comprise at least one ethylenically unsaturated terminal group and a backbone unit comprising an α,β-unsaturated carbonyl. The addition-fragmentation agent is free-radically cleavable. Without intending to be bound by theory, it is surmised that the inclusion of such addition-fragmentation material reduces the polymerization-induced stresses, such as by the mechanism described in U.S. application Ser. No. 13/169,306, filed Jun. 27, 2011. For embodiments wherein the AFM are multifunctional, comprising at least two ethylenically unsaturated group (e.g. Z is ≥2 in Formula I), the material can function as crosslinking agents, where the crosslinks are labile.

The addition-fragmentation agents are preferably of the following formula:

Formula I

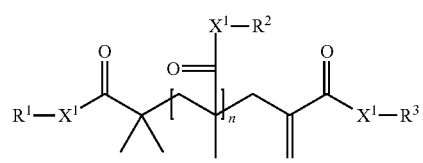

wherein
$R^1$, $R^2$ and $R^3$ are each independently $Z_m$-Q-, a (hetero)alkyl group or a (hetero)aryl group with the proviso that at least one of $R^1$, $R^2$ and $R^3$ is $Z_m$-Q-,
Q is a linking group have a valence of m+1;
Z is an ethylenically unsaturated polymerizable group,
m is 1 to 6, preferably 1 to 2;
each $X^1$ is independently —O— or —$NR^4$—, where $R^4$ is H or $C_1$-$C_4$ alkyl; and
n is 0 or 1.

Addition-fragmentation agents according to Formula I are described in U.S. application Ser. No. 13/169,306, filed Jun. 27, 2011; incorporated herein by reference.

The ethylenically unsaturated moiety, Z, of the monomer may include, but is not limited to the following structures, including (meth)acryloyl, vinyl, styrenic and ethynyl.

In some embodiments, Q is selected from —O—, —S—, —NR$^4$—, —SO$_2$—, —PO$_2$—, —CO—, —OCO—, —R$^6$—, —NR$^4$—CO—NR$^4$—, NR$^4$—CO—O—, NR$^4$—CO—NR$^4$—CO—O—R$^6$—, —CO—NR$^4$—R$^6$—, —R$^6$—CO—O—R$^6$—, —O—R$^6$—, —S—R$^6$—, —NR$^4$—R$^6$—, —SO$_2$—R$^6$—, —PO$_2$—R$^6$—, CO—R$^6$—NR$^4$—CO—R$^6$—, NR$^4$—R$^6$—CO—O—, and NR$^4$—CO—NR$^4$—, wherein each R$^4$ is hydrogen, a C$_1$ to C$_4$ alkyl group, or aryl group, each R$^6$ is an alkylene group having 1 to 6 carbon atoms, a 5- or 6-membered cycloalkylene group having 5 to 10 carbon atoms, or a divalent arylene group having 6 to 16 carbon atoms, with the proviso that Q-Z does not contain peroxidic linkages.

In some embodiments, Q is an alkylene, such as of the formula —C$_r$H$_{2r}$—, where r is 1 to 10. In other embodiments, Q is a hydroxyl-substituted alkylene, such as —CH$_2$—CH(OH)—CH$_2$—. In some embodiments, Q is an aryloxy-substituted alkylene. In some embodiments, R$^5$ is an alkoxy-substituted alkylene.

R$^1$—X$^1$— groups (and optionally R$^2$—X$^2$— groups) is typically selected from H$_2$C=C(CH$_3$)C(O)—O—CH$_2$—CH(OH)—CH$_2$—O—, H$_2$C=C(CH$_3$)C(O)—O—CH$_2$—CH(O—(O)C(CH$_3$)=CH$_2$)—CH$_2$—O—, H$_2$C=C(CH$_3$)C(O)—O—CH(CH$_2$OPh)-CH$_2$—O—, H$_2$C=C(CH$_3$)C(O)—O—CH$_2$CH$_2$—N(H)—C(O)—O—CH(CH$_2$OPh)-CH$_2$—O—, H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(OH)—CH$_2$—O—, H$_2$C=C(CH$_3$)C(O)—O—CH$_2$—CH(O—(O)C—N(H)—CH$_2$CH$_2$—O—(O)C(CH$_3$)C=CH$_2$)—CH$_2$—O—, CH$_3$—(CH$_2$)$_7$—CH(O—(O)C—N(H)—CH$_2$CH$_2$—O—(O)C(CH$_3$)C=CH$_2$)—CH$_2$—O—, H$_2$C=C(H)C(O)—O—(CH$_2$)$_4$—O—CH$_2$—CH(—O—(O)C(H)=CH$_2$)—CH$_2$—O— and H$_2$C=C(H)C(O)—O—CH$_2$—CH(OH)—CH$_2$—O—. H$_2$C=C(H)C(O)—O—(CH$_2$)$_4$—O—CH$_2$—CH(—O—(O)C(H)=CH$_2$)—CH$_2$—O—, and CH$_3$—(CH$_2$)$_7$—CH(O—(O)C—N(H)—CH$_2$CH$_2$—O—(O)C(CH$_3$)C=CH$_2$)—CH$_2$—O—.

The polymerizable resin portion of the hardenable (i.e. polymerizable) dental composition described herein comprises at least 0.5 wt-%, or 1 wt-%, 1.5 wt-%, or 2 wt-% of addition-fragmentation agent(s). The addition-fragmentation agent may comprise a single monomer or a blend of two or more addition-fragmentation agents. The total amount of addition-fragmentation agent(s) in the polymerizable resin portion of the hardenable (i.e. polymerizable) dental composition is typically no greater than 30 wt-%, 25 wt-%, 20 wt-%, or 15 wt-%. As the concentration of the addition-fragmentation monomer increases, the stress deflection and Watts Shrinkage typically decrease. However, when the amount of addition-fragmentation agent exceeds an optimal amount, mechanical properties such as Diametral tensile strength and/or Barcol hardness, or depth of cure may be insufficient.

Materials with high polymerization stress upon curing generate strain in the tooth structure. One clinical consequence of such stress can be a decrease in the longevity of the restoration. The stress present in the composite passes through the adhesive interface to the tooth structure generating cuspal deflection and cracks in the surrounding dentin and enamel which can lead to postoperative sensitivity. Preferred (e.g. filled) dental compositions (useful for restorations such as fillings and crowns) described herein typically exhibit a stress deflection of no greater than 2.0, or 1.8, or 1.6, or 1.4, or 1.2 or 1.0 or 0.8 or 0.6 microns.

In some embodiments, the total amount of addition-fragmentation agent(s) in the polymerizable resin portion of the hardenable (i.e. polymerizable) dental composition is no greater than 14 wt-%, 13 wt-%, or 12 wt-%, or 11 wt-%, or 10 wt-%.

Although a hardenable dental composition comprising an addition fragmentation agent in a low volume shrinkage composition typically provides the lowest stress and/or lowest shrinkage, the fatty mono(meth)acrylate can also improving the handling characteristics of a dental composition comprising conventional hardenable (meth)acrylate monomers.

In some embodiments, the hardenable dental composition comprises at least one conventional hardenable (meth)acrylate monomers such as ethoxylated bisphenol A dimethacrylate (BisEMA6), bisphenol A diglycidyl dimethacrylate (bis-GMA), urethane dimethacrylate (UDMA), and polyethyleneglycol dimethacrylate (PEGDMMA). These monomers were found to phase separate when formed into a mixture with (e.g. 5%, 10%, or 15%) stearyl mono(meth)acrylate. Bulk phase separation is a convenient way of screening the polymerization resin of the hardenable dental composition, or a component thereof, to determine the relative incompatibility.

Although 2-hydroxyethyl methacrylate (HEMA), triethlyene glycol dimethacrylate (TEGDMA), glycerol dimethacrylate (GDMA), and dodecandiol dimethacrylate (DDMA), were found not to phase separate when combined into a mixture with (e.g. 20%) stearyl mono(meth)acrylate, these monomer can also be employed provided the polymerizable resin comprises a sufficient amount of a monomer that does phase separate from the selected fatty mono(meth)acrylate.

The curable component of the curable dental composition can include a wide variety of other ethylenically unsaturated compounds, epoxy-functional (meth)acrylate resins, vinyl ethers, and the like.

The (e.g., photopolymerizable) dental compositions may include free radically polymerizable monomers, oligomers, and polymers having one or more ethylenically unsaturated groups. Suitable compounds contain at least one ethylenically unsaturated bond and are capable of undergoing addition polymerization. Examples of useful ethylenically unsaturated compounds include acrylic acid esters, methacrylic acid esters, hydroxy-functional acrylic acid esters, hydroxy-functional methacrylic acid esters, and combinations thereof. Such free radically polymerizable compounds include mono-,di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1, 4-cyclohexanediol di(meth)acrylate, pentaerythritol tetra(meth)acrylate, sorbitol hex(meth)acrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500); and vinyl compounds such as styrene, diallyl phthalate, divinyl succinate, divinyl adipate and divinyl phthalate. Other suitable free radically polymerizable compounds include siloxane-functional (meth)acrylates. Mixtures of two or more free radically polymerizable compounds can be used if desired.

The curable dental composition may also contain a monomer having hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-ethacryloxypropoxy)phenyl]propane (bisGMA). Suitable ethylenically unsaturated compounds are available from a wide variety of commercial sources, such as Sigma-Aldrich, St. Louis.

The curable dental compositions may include resin-modified glass ionomers cements such as those described in U.S. Pat. No. 5,130,347 (Mitra) U.S. Pat. No. 5,154,762 (Mitra) U.S. Pat. No. 5,962,550 (Akahane). Such compositions can be powder-liquid, paste-liquid or paste-paste systems. Alternatively, copolymer formulations such as those described in U.S. Pat. No. 6,126,922 (Rozzi) are included in the scope of the invention.

An initiator is typically added to the mixture of polymerizable ingredients. The initiator is sufficiently miscible with the resin system to permit ready dissolution in (and discourage separation from) the polymerizable composition. Typically, the initiator is present in the composition in effective amounts, such as from about 0.1 weight percent to about 5.0 weight percent, based on the total weight of the composition.

The addition-fragmentation agent is generally free-radically cleavable. Although photopolymerization is one mechanism for generating free radicals, other curing mechanisms also generate free radicals. Thus, the addition-fragmentation agent does not require irradiation with actinic radiation (e.g. photocuring) in order to provide the reduction in stress during curing.

In some embodiments, the mixture of monomers is photopolymerizable and the composition contains a photoinitiator (i.e., a photoinitiator system) that upon irradiation with actinic radiation initiates the polymerization (or hardening) of the composition. Such photopolymerizable compositions can be free radically polymerizable. The photoinitiator typically has a functional wavelength range from about 250 nm to about 800 nm. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Iodonium salts include diaryl iodonium salts, e.g., diphenyliodonium chloride, diphenyliodonium hexafluorophosphate, and diphenyliodonium tetrafluoroborate. Some preferred photosensitizers may include monoketones and diketones (e.g. alpha diketones) that absorb some light within a range of about 300 nm to about 800 nm (preferably, about 400 nm to about 500 nm) such as camphorquinone, benzil, furil, 3,3,6,6-tetramethylcyclohexanedione, phenanthraquinone and other cyclic alpha diketones. Of these camphorquinone is typically preferred. Preferred electron donor compounds include substituted amines, e.g., ethyl 4-(N,N-dimethylamino)benzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides.

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2, 4, 4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4, 6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Tertiary amine reducing agents may be used in combination with an acylphosphine oxide. Illustrative tertiary amines include ethyl 4-(N,N-dimethylamino)benzoate and N, N-dimethylaminoethyl methacrylate. When present, the amine reducing agent is present in the photopolymerizable composition in an amount from about 0.1 weight percent to about 5.0 weight percent, based on the total weight of the composition. In some embodiments, the curable dental composition may be irradiated with ultraviolet (UV) rays. For this embodiment, suitable photoinitiators include those available under the trade designations IRGACURE and DAROCUR from Ciba Speciality Chemical Corp., Tarrytown, N.Y. and include 1-hydroxy cyclohexyl phenyl ketone (IRGACURE 184), 2,2-dimethoxy-1,2-diphenylethan-1-one (IRGACURE 651), bis(2,4,6-trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl) butanone (IRGACURE 369), 2-methyl-1-[4-(methylthio) phenyl]-2-morpholinopropan-1-one (IRGACURE 907), and 2-hydroxy-2-methyl-1-phenyl propan-1-one (DAROCUR 1173).

The photopolymerizable compositions are typically prepared by admixing the various components of the compositions. For embodiments wherein the photopolymerizable compositions are not cured in the presence of air, the photoinitiator is combined under "safe light" conditions (i.e., conditions that do not cause premature hardening of the composition). Suitable inert solvents may be employed if desired when preparing the mixture. Examples of suitable solvents include acetone and dichloromethane.

Hardening is affected by exposing the composition to a radiation source, preferably a visible light source. It is convenient to employ light sources that emit actinic radiation light between 250 nm and 800 nm (particularly blue light of a wavelength of 380-520 nm) such as quartz halogen lamps, tungsten-halogen lamps, mercury arcs, carbon arcs, low-, medium-, and high-pressure mercury lamps, plasma arcs, light emitting diodes, and lasers. In general, useful light sources have intensities in the range of 0.200-1000 W/cm$^2$. A variety of conventional lights for hardening such compositions can be used.

The exposure may be accomplished in several ways. For example, the polymerizable composition may be continuously exposed to radiation throughout the entire hardening process (e.g., about 2 seconds to about 60 seconds). It is also possible to expose the composition to a single dose of radiation, and then remove the radiation source, thereby allowing polymerization to occur. In some cases materials can be subjected to light sources that ramp from low intensity to high intensity. Where dual exposures are employed, the intensity of each dosage may be the same or different. Similarly, the total energy of each exposure may be the same or different.

The dental compositions comprising the multifunctional ethylenically unsaturated monomers may be chemically hardenable, i.e., the compositions contain a chemical initiator (i.e., initiator system) that can polymerize, cure, or otherwise harden the composition without dependence on irradiation with actinic radiation. Such chemically hardenable (e.g., polymerizable or curable) composition are sometimes referred to as "self-cure" compositions and may include redox cure systems. Further, the polymerizable composition may comprise a combination of different initiators, at least one of which is suitable for initiating free radical polymerization.

The chemically hardenable compositions may include redox cure systems that include a polymerizable component (e.g., an ethylenically unsaturated polymerizable component) and redox agents that include an oxidizing agent and a reducing agent.

The reducing and oxidizing agents react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical conditions.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state.

In favored embodiments, such as when the dental composition is employed as a dental restorative (e.g. dental filling or crown) or an orthodontic cement, the dental composition typically comprises appreciable amounts of (e.g. nanoparticle) filler. Such compositions preferably include at least 40 wt-%, more preferably at least 45 wt-%, and most preferably at least 50 wt-% filler, based on the total weight of the composition. In some embodiments the total amount of filler is at most 90 wt-%, preferably at most 80 wt-%, and more preferably at most 75 wt-% filler.

The (e.g. filled) dental composite materials typically exhibit a diametral tensile strength (DTS) of at least about 70, 75, or 80 MPa and/or a Barcol Hardness of at least about 60, or 65, or 70-. The depth of cure ranges from about 4 to about 5 and comparable to commercially available (e.g. filled) dental compositions suitable for restorations.

Dental compositions suitable for use as dental adhesives can optionally also include filler in an amount of at least 1 wt-%, 2 wt-%, 3 wt-%, 4 wt-%, or 5 wt-% based on the total weight of the composition. For such embodiments, the total concentration of filler is at most 40 wt-%, preferably at most 20 wt-%, and more preferably at most 15 wt-% filler, based on the total weight of the composition.

Fillers may be selected from one or more of a wide variety of materials suitable for incorporation in compositions used for dental applications, such as fillers currently used in dental restorative compositions, and the like.

The filler can be an inorganic material. It can also be a crosslinked organic material that is insoluble in the polymerizable resin, and is optionally filled with inorganic filler. The filler is generally non-toxic and suitable for use in the mouth. The filler can be radiopaque, radiolucent, or nonradiopaque. Fillers as used in dental applications are typically ceramic in nature.

Non-acid-reactive inorganic filler particles include quartz (i.e., silica), submicron silica, zirconia, submicron zirconia, and non-vitreous microparticles of the type described in U.S. Pat. No. 4,503,169 (Randklev).

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.) and U.S. Pat. No. 7,156,911; and U.S. Pat. No. 7,649,029 (Kolb et al.).

Examples of suitable organic filler particles include filled or unfilled pulverized polycarbonates, polyepoxides, poly(meth)acrylates and the like. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles, in particular the uniformity of the shape.

Micron-size particles are very effective for improving post-cure wear properties. In contrast, nanoscopic fillers are commonly used as viscosity and thixotropy modifiers. Due to their small size, high surface area, and associated hydrogen bonding, these materials are known to assemble into aggregated networks.

In some embodiments, the dental composition preferably comprise a nanoscopic particulate filler (i.e., a filler that comprises nanoparticles) having an average primary particle size of less than about 0.100 micrometers (i.e., microns), and more preferably less than 0.075 microns. As used herein, the term "primary particle size" refers to the size of a non-associated single particle. The average primary particle size can be determined by cutting a thin sample of hardened dental composition and measuring the particle diameter of about 50-100 particles using a transmission electron micrograph at a magnification of 300,000 and calculating the average. The filler can have a unimodal or polymodal (e.g., bimodal) particle size distribution. The nanoscopic particulate material typically has an average primary particle size of at least about 2 nanometers (nm), and preferably at least about 7 nm. Preferably, the nanoscopic particulate material has an average primary particle size of no greater than about 50 nm, and more preferably no greater than about 20 nm in size. The average surface area of such a filler is preferably at least about 20 square meters per gram ($m^2/g$), more preferably, at least about 50 $m^2/g$, and most preferably, at least about 100 $m^2/g$.

In some preferred embodiments, the dental composition comprises silica nanoparticles. Suitable nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Surface & Colloid Science, Vol. 6, ed. Matijevic, E., Wiley Interscience, 1973. Preferred silica sols for use making the fillers are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E.I. Dupont de Nemours & Co. or Nalco 2326 from Nalco Chemical Co.).

Preferably, the silica particles in the sol have an average particle diameter of about 5-100 nm, more preferably 10-50 nm, and most preferably 12-40 nm. A particularly preferred silica sol is NALCO 1041.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, lower refractive index (e.g. silica) nanoparticles are employed in combination with high refractive index (e.g. zirconia) nanoparticles in order to index match (refractive index within 0.02) the filler to the refractive index of the polymerizable resin.

In some embodiments, the nanoparticles are in the form of nanoclusters, i.e. a group of two or more particles associated by relatively weak intermolecular forces that cause the particles to clump together, even when dispersed in a hardenable resin.

Preferred nanoclusters can comprise a substantially amorphous cluster of non-heavy (e.g. silica) particles, and amorphous heavy metal oxide (i.e. having an atomic number greater than 28) particles such as zirconia. The particles of the nanocluster preferably have an average diameter of less than about 100 nm. Suitable nanocluster fillers are described in U.S. Pat. No. 6,730,156 (Windisch et al.); incorporated herein by reference.

In some preferred embodiments, the dental composition comprises nanoparticles and/or nanoclusters surface treated with an organometallic coupling agent to enhance the bond between the filler and the resin. The organometallic coupling agent may be functionalized with reactive curing groups, such as acrylates, methacrylates, vinyl groups and the like.

Suitable copolymerizable organometallic compounds may have the general formulas: $CH_2=C(CH_3)_m Si(OR)_n$ or $CH_2=C(CH_3)_m C=OOASi(OR)_n$; wherein m is 0 or 1, R is an alkyl group having 1 to 4 carbon atoms, A is a divalent organic linking group, and n is from 1 to 3. Preferred coupling agents include gamma-methacryloxypropyltrimethoxysilane, gamma-mercaptopropyltriethoxysilane, gamma-aminopropyltrimethoxysilane, and the like.

In some embodiments, a combination of surface modifying agents can be useful, wherein at least one of the agents has a functional group co-polymerizable with a hardenable resin. Other surface modifying agents which do not generally react with hardenable resins can be included to enhance dispersibility or rheological properties. Examples of silanes of this type include, for example, aryl polyethers, alkyl, hydroxy alkyl, hydroxy aryl, or amino alkyl functional silanes.

The surface modification can be done either subsequent to mixing with the monomers or after mixing. It is typically preferred to combine the organosilane surface treatment compounds with nanoparticles before incorporation into the resin. The required amount of surface modifier is dependant upon several factors such as particle size, particle type, modifier molecular wt, and modifier type. In general it is preferred that approximately a monolayer of modifier is attached to the surface of the particle.

The surface modified nanoparticles can be substantially fully condensed. Fully condensed nanoparticles (with the exception of silica) typically have a degree of crystallinity (measured as isolated metal oxide particles) greater than 55%, preferably greater than 60%, and more preferably greater than 70%. For example, the degree of crystallinity can range up to about 86% or greater. The degree of crystallinity can be determined by X-ray diffraction techniques. Condensed crystalline (e.g. zirconia) nanoparticles have a high refractive index whereas amorphous nanoparticles typically have a lower refractive index.

In some embodiments, the dental compositions can have an initial color remarkably different than the cured dental structures. Color can be imparted to the composition through the use of a photobleachable or thermochromic dye. As used herein, "photobleachable" refers to loss of color upon exposure to actinic radiation. The composition can include at least 0.001 wt-% photobleachable or thermochromic dye, and typically at least 0.002 wt-% photobleachable or thermochromic dye, based on the total weight of the composition. The composition typically includes at most 1wt-% photobleachable or thermochromic dye, and more typically at most 0.1 wt-% photobleachable or thermochromic dye, based on the total weight of the composition. The amount of photobleachable and/or thermochromic dye may vary depending on its extinction coefficient, the ability of the human eye to discern the initial color, and the desired color change. Suitable thermochromic dyes are disclosed, for example, in U.S. Pat. No. 6,670,436 (Burgath et al.).

For embodiments including a photobleachable dye, the color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. The photobleachable dye is generally at least partially soluble in a hardenable resin.

Photobleachable dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change can be initiated by actinic radiation such as provided by a dental curing light which emits visible or near infrared (IR) light for a sufficient amount of time. The mechanism that initiates the color change in the compositions may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

Optionally, compositions may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions can contain additives such as indicators, dyes, pigments, inhibitors, accelerators, viscosity modifiers, wetting agents, buffering agents, radical and cationic stabilizers (for example BHT,), and other similar ingredients that will be apparent to those skilled in the art.

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combinations of any of the above additives may also be employed. The selection and amount of any one such additive can be selected by one of skill in the art to accomplish the desired result without undue experimentation.

The curable dental composition can be used to treat an oral surface such as tooth, as known in the art. In some embodiments, the compositions can be hardened by curing after applying the dental composition. For example, when the curable dental composition is used as a restorative such as a dental filling, the method generally comprises applying the curable composition to an oral surface (e.g. cavity); and curing the composition. In some embodiments, a dental adhesive may be applied prior to application of the curable dental restoration material described herein. Dental adhesives are also typically hardened by curing concurrently with curing the highly filled dental restoration composition. The method of treating an oral surface may comprise providing a dental article and adhering the dental article to an oral (e.g. tooth) surface.

In other embodiments, the compositions can be hardened (e.g., polymerized) into dental articles prior to applying. For example, a dental article such as a crown may be pre-formed from the hardenable dental composition described herein. Dental composite (e.g. crowns) articles can be made from the curable composition described herein by casting the curable composition in contact with a mold and curing the composition. Alternatively, dental composite (e.g. crowns) article can be made by first curing the composition forming a mill blank and then mechanically milling the composition into the desired article.

Another method of treating a tooth surface comprises providing a dental composition as described herein wherein the composition is in the form of a (partially hardened) hardenable, self-supporting, malleable structure having a first semi-finished shape; placing the hardenable dental composition on a tooth surface in the mouth of a subject; customizing the shape of the hardenable dental composition; and hardening the hardenable dental composition. The customization can occur in the patient's mouth or on a model outside the patient mouth such as described in U.S. Pat. No. 7,674,850 (Karim et al.); incorporated herein by reference.

Objects and advantages are further illustrated by the following examples, but the particular materials and amounts thereof recited in these examples, as well as other conditions and details, should not be construed to unduly limit this invention. Unless otherwise indicated, all parts and percentages are on a weight basis.

EXAMPLES

| | |
|---|---|
| DDMA (Dodecanediol Dimethacrylate) | Sigma-Aldrich (St. Louis, MO) |
| Stearyl Methacrylate | TCI America (Portland, OR) |
| Lauryl Methacrylate | Sigma-Aldrich |
| Methyl Methacrylate | Sigma-Aldrich |
| Pentyl Methacrylate | Sigma-Aldrich |
| CPQ (camphorquinone) | Sigma-Aldrich |
| EDMAB (ethyl 4-(N,N-dimethylamino) benzoate) | Sigma-Aldrich |
| DPIHFP (diphenyl iodonium hexafluorophosphate) | Alpha Aesar (Ward Hill, MA) |
| BHT (butylated hydroxytoluene) | Sigma-Aldrich |
| YbF$_3$ (Ytterbium Fluoride), 100 nanometer | Sukgyung AT Co. Ltd., Korea |
| Silica filler | Refers to a silane treated nano-sized silica having a nominal particle size of approximately 20 nanometers, prepared essentially as described for Filler F in US Patent Publication No. 2005/0252413 |
| Zirconia filler | Refers to a silane treated nano-sized zirconia prepared essentially as described in Preparatory Example 1A in US Patent Publication No. 2005/0252413 |
| Zr—Si filler | Refers to silane treated zirconia-silica nanocluster filler prepared essentially as described in Preparatory Examples A and B in U.S. Pat. No. 6,730,156 |

Synthesis of Fatty Mono(meth)acrylate
Preparation of Branched C20 Methacrylate

In a flask was mixed 100.0 g of Isofol 20 (Sasol), 59.46 g of methacrylic anhydride (Monomer and Polymer Dajac Lab), 1.0 g of 4-dimethylamino pyridine (Aldrich), and 100 mL of ethyl acetate. The mixture was stirred at 60° C. for 17 hours, then for an additional 7 hours at 90° C. The mixture was diluted with 200 mL of ethyl acetate, then washed with 1.0 M HCl, and 1.0 M NaOH. The organic layer was then concentrated under vacuum. The crude oil was mixed with an equal portion of hexane and passed through a column of neutral alumina to remove colored impurities. The alumina was eluted with hexane. The collected fractions were concentrated under vacuum to give the final product, depicted as follows, as a colorless oil.

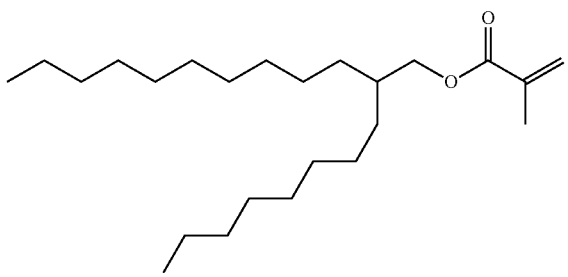 [SMILES: C=C(C)C(=O)OCC(CCCCCCCC)CCCCCCCCCC]

Preparation of Branched C18 Acrylate

A mixture of 197.17 g of Isofol 18T (Sasol), 78.12 g of triethylamine (TEA, Alfa Aesar), and 700 g of methylene chloride (MC) was cooled to 5° C. using an ice bath. 69.86 g of acryloyl chloride (AC, Alfa Aesar) was added dropwise over one hour with mechanical stirring. After 10 hours, the mixture was filtered, then concentrated under vacuum. The remaining oil was diluted with ethyl acetate and washed with 1.0 M HCl, 1.0 M NaOH, and brine. The organic layer was then concentrated under vacuum. The crude oil was mixed with an equal potion of hexane and passed through a column of neutral alumina to remove colored impurities. The alumina was eluted with hexane. The collected filtrate was concentrated under vacuum to give the final product as a colorless oil.

This gives a mixture of acrylate isomers as follows wherein the average alkyl group is C18.

2-hexyl-1-decyl acrylate, 2-octyl-1-decyl acrylate, 2-hexyl-1-dodecyl acrylate, 2-octyl-1-dodecyl acrylate Synthesis of Polymerizable Monomers 1. Synthesis of Addition Fragmentation Agent (AFM-1)

Distillation of Methyl Methacrylate Oligomer Mixture

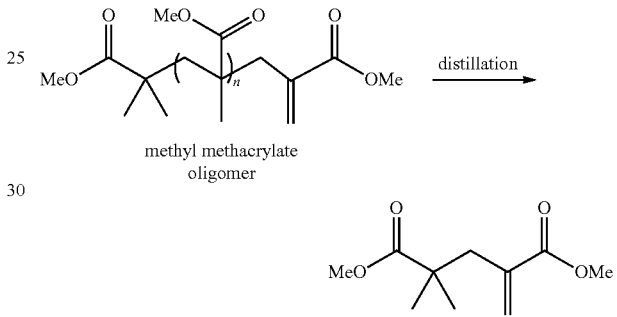

Distillation was performed as described in Moad, C. L.; Moad, G.; Rizzardo, E.; and Thang, S. H. *Macromolecules*, 1996, 29, 7717-7726, with details as follows: A 1 L round-bottomed flask equipped with a magnetic stir bar was charged with 500 g of methyl methacrylate oligomer mixture. The flask was fitted with a Vigreux column, a condenser, a distribution adapter, and four collection flasks. With stirring, the distillation apparatus was placed under reduced pressure (0.25 mm Hg). The oligomer mixture was stirred under reduced pressure at room temperature until gas evolution (removal of methyl methacrylate monomer) had largely subsided. The distillation pot was then heated to reflux in an oil bath to distill the oligomer mixture. The fractions isolated by this procedure are listed in Table 1.

TABLE 1

Fractions from the Distillation of Methyl Methacrylate Oligomer Mixture

| Fraction | Pressure (mm Hg) | Boiling point (° C.) | Mass (g) | Approximate Composition |
|---|---|---|---|---|
| A | 0.25 | 59 | 63.27 | Dimer |
| B | 0.09 | 47 | 115.97 | Dimer |
| C | 0.10 | 60-87 | 25.40 | dimer (~50-75%), oligomers (mainly trimer) |
| D | 0.10 | 87 | 15.20 | dimer (~5%), oligomers (mainly trimer) |
| E | 0.13 | 105 | 156.66 | oligomers (trimer and higher) |

Hydrolysis of Methyl Methacrylate Dimer

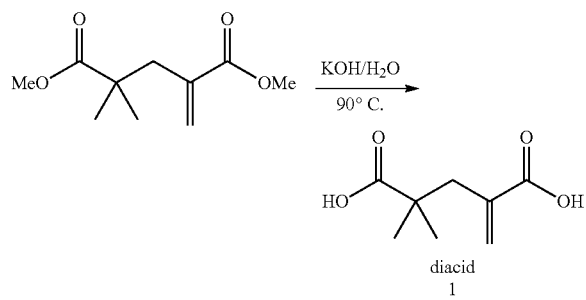

Hydrolysis of the dimer to Diacid 1 was performed as described in Hutson, L.; Krstina, J.; Moad, G.; Morrow, G. R.; Postma, A.; Rizzardo, E.; and Thang, S. H. *Macromolecules*, 2004, 37, 4441-4452, with details as follows: A 1 L, round-bottomed flask equipped with a magnetic stir bar was charged with deionized water (240 mL) and potassium hydroxide (60.0 g, 1007 mmol). The mixture was stirred until homogeneous. Methyl methacrylate dimer (75.0 g, 374.6 mmol) was added. The reaction was equipped with a reflux condenser and was heated to 90° C. in an oil bath. After 17 hours, the reaction was removed from the oil bath and was allowed to cool to room temperature. The reaction solution was acidified to pH of approximately 1 using concentrated HCl. A white precipitate formed upon acidification. The heterogeneous mixture was vacuum filtered and quickly washed twice with 50-100 mL of deionized water. The white solid was dried by pulling air through the solid for approximately 4 hours. The white solid was then dissolved in approximately 1750 mL of dichloromethane. Only a very small amount (less than a gram) of solid remained insoluble. The solution was allowed to stand for 24 hours. The dichloromethane solution was then vacuum filtered to remove the undissolved white solid. The filtered dichloromethane solution was concentrated in vacuo to provide a white solid. The solid was further dried under high vacuum to provide Diacid 1 (55.95 g, 325.0 mmol, 87%) as a white powder.

Preparation of AFM-1

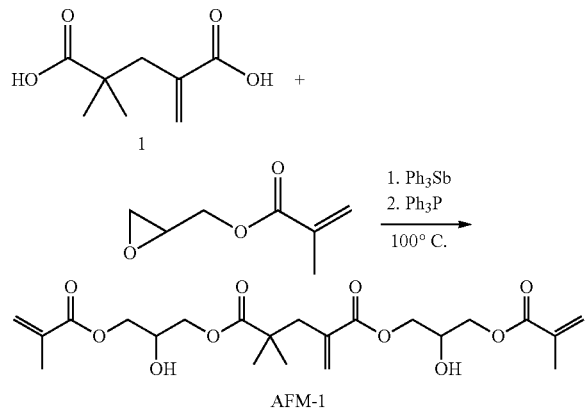

An approximately 250 mL amber bottle equipped with a magnetic stir bar was charged with glycidyl methacrylate (23.0 mL, 24.8 g, 174 mmol) and triphenyl antimony (0.369 g, 1.04 mmol). The reaction was covered with a plastic cap with two 16 gauge needles pierced through the cap to allow air into the reaction. With stirring, the mixture was heated to 100° C. in an oil bath. Diacid 1 (15.0 g, 87.1 mmol) was added to the reaction in small portions over a period of 1.5 hours. After 21 hours, triphenyl phosphine (0.091 g, 0.35 mmol) was added. The reaction was kept stirring at 100° C. After an additional 6.5 hours the reaction was sampled, and 1H NMR analysis was consistent with the desired product as a mixture of isomers and indicated consumption of glycidyl methacrylate. The reaction was cooled to room temperature to provide AFM-1 as a clear, very pale yellow viscous material.

2. Synthesis of Isocyanurate Trimer

Phthalic acid anhydride (57.0 g, 0.385 mol, CAS #85-33-9, Alfa Aesar, lot G30T004), 4-(dimethylamino)pyridine (DMAP, 4.9 g, 0.04 mol, CAS #1122-58-3, Alfa Aesar, lot L125009), 2-hydroxyethylmethacrylate (HEMA, 50.9 g, 0.391 mol, and butylated hydroxytoluene (BHT, 0.140 g) were charged into a 2-liter 3-neck reaction flask equipped with a mechanical stirrer, a thermocouple connected to a temperature controller, a dry air stream running through a T-shape connection into the reactor then to an oil bubbler, and a heating mantle. With continuous stirring, the flask contents were heated to 95° C., by which all components dissolved and a clear liquid was obtained. Heating at 95° C. and stirring were continued for 5 hours. The heat was turned off and the flask contents were allowed to cool to room temperature while still being stirred under dry air. Acetone (250 ml) was added followed by tris-(2-hydroxyethyl)isocyanurate (33.58 g, 0.158 mol, from TCI). The heating mantle was replaced with an ice bath, where the mixture was cooled to 0-5° C. A solution made from dicyclohexyl carbodiimide (DCC, 81 g, 0.393 mol) in 120 ml acetone was placed into a 500 ml dropping funnel which was placed in-between the reaction flask and the dry air in-let. The DCC solution was added slowly to the continuously stirred reaction mixture in a rate where the reaction mixture temperature would not exceed 10° C. After complete addition of the DCC solution, the reaction was stirred in the ice bath for 2 hours in at room temperature overnight. On day 2, the solid formed was removed by vacuum filtration and the residue was concentrated in a rotary evaporator at 40-45° C. bath. The residue was dissolved in 300 ml solution of ethylacetate: hexanes, 2:1 by volume. The obtained solution was extracted with 200 ml of 1.0 N. HCl, 200 ml of 10% aqueous, 200 ml H₂O, and 200 ml brine. The organic layer was concentrated in a rotary evaporator with 40° C. bath. Further drying was done under a vacuum pump at 50° C. for 3 hours with air bleeding into the product during the whole time to give an almost colorless hazy viscous liquid.

The refractive index was measured and found to be 1.5386. By use of NMR the liquid was determined to be the product shown is the following reaction scheme.

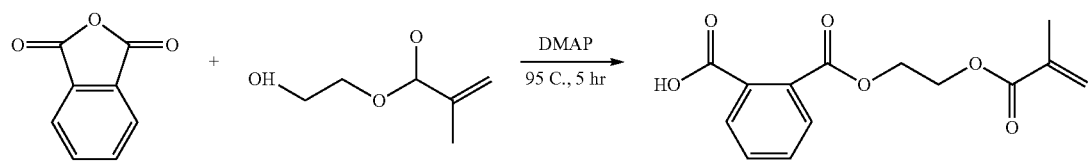

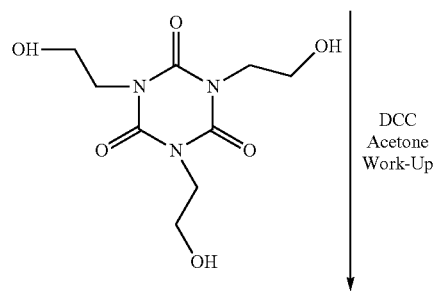

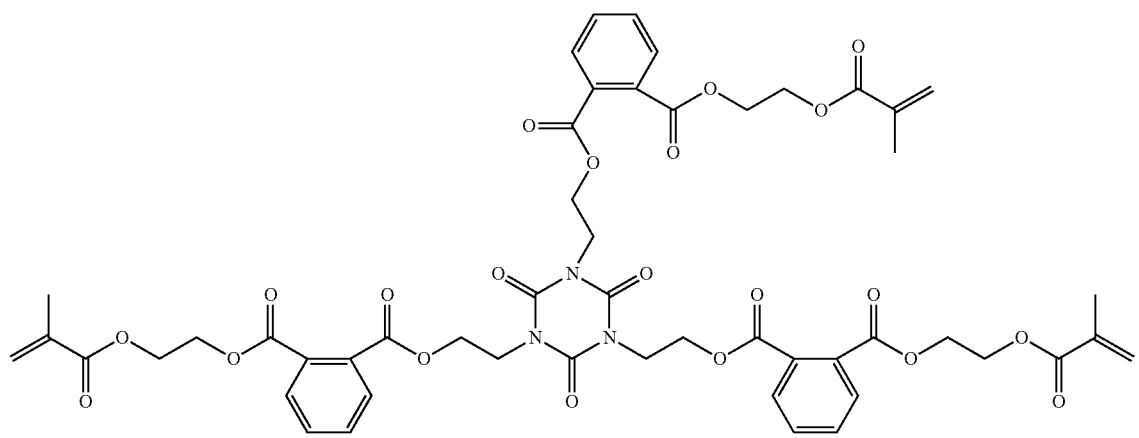

The calculated molecular weight of the depicted end product was determined to be 1041 g/mole.

3. ERGP-IEM was made as described in WO2012/003136

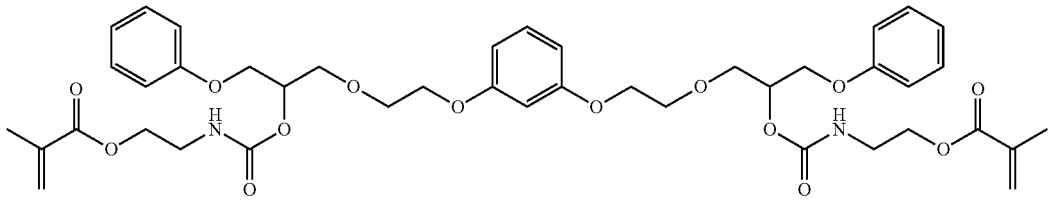

Mw = 808.9; $n_D^{20}$ = 1.539; η = 435 Pa*s

Test Methods

Diametral Tensile Strength (DTS) Test Method

Diametral tensile strength of a test sample was measured according to the following procedure. An uncured composite sample was injected into a 4-mm (inside diameter) glass tube; the tube was capped with silicone rubber plugs. The tube was compressed axially at approximately 2.88 kg/cm² pressure for 5 minutes. The sample was then light cured for 80 seconds by exposure to a XL 1500 dental curing light (3M Company, St. Paul, Minn.), followed by irradiation for 90 seconds in a Kulzer UniXS curing box (Heraeus Kulzer GmbH, Germany). The sample was cut with a diamond saw to form disks about 2 mm thick, which were stored in distilled water at 37° C. for about 24 hours prior to testing. Measurements were carried out on an Instron tester (Instron 4505, Instron Corp., Canton, Mass.) with a 10 kilonewton (kN) load cell at a crosshead speed of 1 mm/minute according to ISO Specification 7489 (or American Dental Association (ADA) Specification No. 27). Samples were prepared and measured with results reported in MPa as the average of multiple measurements.

Depth of Cure Test Method

The depth of cure was determined by filling a 10 or 15 millimeter stainless steel mold cavity with the composite, covering the top and bottom of the mold with sheets of polyester film, pressing the sheets to provide a leveled composition surface, placing the filled mold on a white background surface, irradiating the dental composition for 20 seconds using a dental curing light (3M Dental Products Curing Light 2500 or 3M ESPE Elipar FreeLight2, 3M ESPE Dental Products), separating the polyester films from each side of the mold, gently removing (by scraping) materials from the bottom of the sample (i.e., the side that was not irradiated with the dental curing light), and measuring the thickness of the remaining material in the mold. The reported depths are the actual cured thickness in millimeters divided by 2.

Extrusion Force Test Method

Extrusion force was tested using an Instron Model 4505 (Instron Corp., Canton, Mass.) and a crosshead speed of 51 mm/min. A cylindrical nylon capsule having internal dimensions of 4.0 mm diameter by 23.0 mm length and having an angled dispensing tip with an internal diameter of 2.0 mm and length of 6.8 mm was loaded with a composite paste, a plunger was inserted into the capsule, and the assembled capsule was loaded into a sample holder such that the capsule body was supported on the stationary jaw and the plunger was pushed by the moveable jaw. As the plunger was pushed into the capsule, the maximum load (extrusion force) required while pushing the plunger into the capsule was measured in units of kilogram-force (Kg-F).

Contrast Ratio

Paste samples were formed into 1 mm thick by 20 mm diameter disks and cured by exposing them to illumination from an LED array (455 nm wavelength, 800 mW/cm$^2$ intensity) for 20 seconds on one side of the disk. ASTM-D2805-95 test method was modified to measure the Contrast Ratio (or opacity) of the disks. Y-tristimulus values for the disks were measured on an Ultrascan XE Colorimeter (Hunter Associates Laboratory, Reston, Va.) with a 0.953-cm aperture using separate white and black backgrounds. The D65 Illuminant was used with no filters for all measurements. A 10 degree angle of view was used. The Contrast Ratio, CR, was calculated as the ratio of the reflectance through a material on a black substrate to the reflectance through an identical material on a white substrate. Reflectance is defined as equal to the Y-tristimulus value. Thus, CR=RB/RW, where RB=reflectance through a sample on a black substrate and RW=reflectance through the same sample on a white substrate. Reported Contrast Ratio values are from single measurements with lower values indicative of greater translucency (i.e., transmission of light).

Polymerizable Resin Compositions Examples 1A-2A

| | grams, (wt % of polymerizable resin, wt % of total hardenable composition including filler) | | |
|---|---|---|---|
| Component | Comparative resin | Resin for Example 1A | Resin for Example 2A |
| Stearyl methacrylate | 0.0000 (0.00, 0.00) | 0.9828 (4.90, 1.76) | 1.9646 (4.91, 1.31) |
| Trimer | 18.362 (30.52, 11.60) | 5.6668 (28.28, 10.18) | 11.6448 (29.11, 7.79) |
| ERGP-IEM | 35.938 (59.73, 22.70) | 11.500 (57.39, 20.66) | 23.2895 (58.22, 15.59) |
| DDMA | 3.827 (6.36, 2.42) | 1.185 (5.91, 2.13) | 2.3551 (5.89, 1.58) |
| BHT | 0.0322 (0.05, 0.02) | 0.0126 (0.06, 0.02) | 0.0199 (0.05, 0.01) |
| AFM-1 | 0.911 (1.51, 0.57) | 0.326 (1.63, 0.59) | 0.0000 (0.00, 0.00) |
| CPQ | 0.1922 (0.32, 0.12) | 0.0646 (0.32, 0.12) | 0.1279 (0.32, 0.09) |
| EDMAB | 0.6039 (1.00, 0.38) | 0.1996 (1.00, 0.36) | 0.3998 (1.00, 0.27) |
| DPIHFP | 0.3051 (0.51, 0.19) | 0.1002 (0.50, 0.18) | 0.1990 (0.50, 0.13) |

Dental Restoration Composition Examples 1B-2B

| | grams, (wt % of total hardenable composition including filler) | | |
|---|---|---|---|
| Component | Comparative | Example 1B | Example 2B |
| Comparative resin | 2.8651 (38.01) | 0.0000 (0.00) | 0.0000 (0.00) |
| Resin for Example 1 | 0.0000 (0.00) | 7.20 (36.00) | 0.0000 (0.00) |
| Resin for Example 2 | 0.0000 (0.00) | 0.0000 (0.00) | 5.361 (26.77) |
| YbF$_3$ | 0.3501 (4.64) | 0.96 (4.80) | 1.0973 (5.48) |
| Silica filler | 0.2734 (3.63) | 0.4995 (2.50) | 0.5719 (2.86) |
| Zirconia filler | 0.1464 (1.94) | 0.2695 (1.35) | 0.3317 (1.66) |
| Zr/Si filler | 3.9036 (51.78) | 11.0723 (55.36) | 12.6679 (63.25) |

Handling Test Results for Examples 1-2

Comparative paste: a dental instrument would push into the material and stick, rather than moving the material. The paste was extremely sticky and would string with the instrument, often over an inch when the instrument was pulled back.

Example 1 paste: The material could be moved by an instrument, could be shaped, allowing anatomy to be formed in the paste before curing. The stringing and tackiness were both substantially reduced.

Example 2 paste: This paste was a universal composite, rather than a flowable, because of the % filler loading. The paste had exceptional ability to feather, or thin to a fine layer with a dental instrument, it held its shape after manipulation, and had a high surface gloss. The stringing and tackiness were both substantially reduced.

Dental Restoration Composition Examples 3-6

| | | grams, (wt-% of total composition including filler) | | | |
|---|---|---|---|---|---|
| Component | Comparative (grams) | Example 3 | Example 4 | Example 5 | Example 6 |
| Stearyl methacrylate | 0.0000 (0.00) | 0.1081 (0.54) | 0.1622 (0.81) | 0.2162 (1.08) | 0.2703 (1.35) |
| Trimer | 1.6448 (8.22) | 1.6119 (8.05) | 1.5955 (7.97) | 1.5790 (7.89) | 1.5626 (7.81) |
| ERGP-IEM | 3.2355 (16.17) | 3.1708 (15.84) | 3.1384 (15.68) | 3.1061 (15.52) | 3.0737 (15.36) |
| DDMA | 0.3446 (1.72) | 0.3377 (1.69) | 0.3343 (1.67) | 0.3308 (1.65) | 0.3274 (1.64) |
| BHT | 0.0027 (0.01) | 0.0026 (0.01) | 0.0026 (0.01) | 0.0026 (0.01) | 0.0026 (0.01) |
| AFM-1 | 0.0797 (0.40) | 0.0781 (0.39) | 0.0773 (0.39) | 0.0765 (0.38) | 0.0757 (0.38) |
| CPQ | 0.0174 (0.09) | 0.0171 (0.09) | 0.0169 (0.08) | 0.0167 (0.08) | 0.0165 (0.08) |
| EDMAB | 0.0541 (0.27) | 0.0530 (0.26) | 0.0525 (0.26) | 0.0519 (0.26) | 0.0514 (0.26) |
| DPIHFP | 0.0270 (0.13) | 0.0265 (0.13) | 0.0262 (0.13) | 0.0259 (0.13) | 0.0257 (0.13) |
| $YbF_3$ | 1.0955 (5.48) | 1.10 (5.50) | 1.10 (5.50) | 1.10 (5.50) | 1.10 (5.50) |
| Silica filler | 0.5696 (2.85) | 0.57 (2.85) | 0.57 (2.85) | 0.57 (2.85) | 0.57 (2.85) |
| Zirconia filler | 0.3061 (1.53) | 0.31 (1.55) | 0.31 (1.55) | 0.31 (1.55) | 0.31 (1.55) |
| Zr/Si filler | 12.6295 (63.13) | 12.63 (63.10) | 12.63 (63.10) | 12.63 (63.10) | 12.63 (63.10) |

Test Results for Examples 3-6

| Composition | Contrast Ratio |
|---|---|
| Comparative | 35.31 |
| Example 3 | 37.16 |
| Example 4 | 46.26 |
| Example 5 | 51.77 |
| Example 6 | 56.31 |

Polymerizable Resin Composition Examples 7-12 all Quantities are in Grams

| Component | Comp. 0.0000 No fatty mono (meth) acrylate | Ex. 7 0.2703 Methyl meth acrylate | Ex. 8 0.2703 Pentyl meth acrylate | Ex. 9 0.2703 Lauryl meth acrylate | Ex. 10 0.2703 Stearyl meth acrylate | Ex. 11 0.2703 Branched C18 Acrylate | Ex. 12 0.2703 Branched C20 Methacrylate |
|---|---|---|---|---|---|---|---|
| Trimer | 1.6448 | 1.5626 | 1.5626 | 1.5626 | 1.5626 | 1.5626 | 1.5626 |
| ERGP-IEM | 3.2355 | 3.0737 | 3.0737 | 3.0737 | 3.0737 | 3.0737 | 3.0737 |
| DDMA | 0.3446 | 0.3274 | 0.3274 | 0.3274 | 0.3274 | 0.3274 | 0.3274 |
| BHT | 0.0027 | 0.0026 | 0.0026 | 0.0026 | 0.0026 | 0.0026 | 0.0026 |
| AFM-1 | 0.0797 | 0.0793 | 0.0793 | 0.0793 | 0.0793 | 0.0793 | 0.0793 |
| CPQ | 0.0174 | 0.0165 | 0.0165 | 0.0165 | 0.0165 | 0.0165 | 0.0165 |
| EDMAB | 0.0541 | 0.0514 | 0.0514 | 0.0514 | 0.0514 | 0.0514 | 0.0514 |
| DPIHFP | 0.0270 | 0.0256 | 0.0256 | 0.0256 | 0.0256 | 0.0256 | 0.0256 |

The polymerizable resin mixtures (i.e. without filler) were thoroughly mixed at elevated temperatures and allowed to cool to room temperature, observing phase separation behavior. Phase separation was seen in Examples 10-12, while no phase separation was seen in Examples 7 and 8. In the case of Example 9, comprising lauryl methacrylate, the mixture needed cooling to 5 degrees C. to observe phase separation.

Dental Restoration Composition Examples 13-20

| | | | | grams, (wt % of total composition including filler) | | | | | |
|---|---|---|---|---|---|---|---|---|---|
| Component | Comp. Ex. | Ex. 13 | Ex. 14 | Ex. 15 | Ex. 16 | Ex. 17 | Ex. 18 | Ex. 19 | Ex. 20 |
| Fatty mono methacrylate | 0.0000 (0.00) | 0.2725 (1.36) Stearyl | 0.5404 (2.70) Stearyl | 0.8100 (4.05) Stearyl | 1.0839 (5.42) Stearyl | 0.2745 (1.37) Lauryl | 0.5383 (2.69) Lauryl | 0.8051 (4.03) Lauryl | 1.0722 (5.36) Lauryl |

-continued

| Component | Comp. Ex. | Ex. 13 | Ex. 14 | Ex. 15 | Ex. 16 | Ex. 17 | Ex. 18 | Ex. 19 | Ex. 20 |
|---|---|---|---|---|---|---|---|---|---|
| Trimer | 1.6448 (8.22) | 1.5580 (7.79) | 1.4751 (7.38) | 1.3934 (6.96) | 1.3107 (6.55) | 1.5610 (7.80) | 1.4757 (7.38) | 1.3925 (6.96) | 1.3083 (6.55) |
| ERGP-IEM | 3.2355 (16.17) | 3.0648 (15.33) | 2.9017 (14.51) | 2.7410 (13.70) | 2.5783 (12.88) | 3.0708 (15.35) | 2.9029 (14.52) | 2.7392 (13.70) | 2.5737 (12.88) |
| DDMA | 0.3446 (1.72) | 0.3264 (1.63) | 0.3091 (1.55) | 0.2919 (1.46) | 0.2746 (1.37) | 0.3271 (1.63) | 0.3092 (1.55) | 0.2917 (1.46) | 0.2741 (1.37) |
| BHT | 0.0027 (0.01) | 0.0026 (0.01) | 0.0024 (0.01) | 0.0023 (0.01) | 0.0022 (0.01) | 0.0026 (0.01) | 0.0024 (0.01) | 0.0023 (0.01) | 0.0021 (0.01) |
| AFM-1 | 0.0797 (0.40) | 0.0755 (0.38) | 0.0715 (0.36) | 0.0675 (0.34) | 0.0635 (0.32) | 0.0756 (0.38) | 0.0715 (0.36) | 0.0675 (0.34) | 0.0634 (0.32) |
| CPQ | 0.0174 (0.09) | 0.0172 (0.09) | 0.0173 (0.09) | 0.0173 (0.09) | 0.0173 (0.09) | 0.0174 (0.09) | 0.0173 (0.09) | 0.0173 (0.09) | 0.0173 (0.09) |
| EDMAB | 0.0541 (0.27) | 0.0541 (0.27) | 0.0539 (0.27) | 0.0540 (0.27) | 0.0539 (0.27) | 0.0541 (0.27) | 0.0541 (0.27) | 0.0538 (0.27) | 0.0539 (0.27) |
| DPIHFP | 0.0270 (0.13) | 0.0270 (0.14) | 0.0269 (0.13) | 0.0269 (0.13) | 0.0271 (0.14) | 0.0270 (0.13) | 0.0268 (0.13) | 0.0270 (0.14) | 0.0270 (0.14) |
| YbF$_3$ | 1.0955 (5.48) | 1.0900 (5.45) | 1.0967 (5.48) | 1.0995 (5.50) | 1.0950 (5.47) | 1.0951 (5.47) | 1.0950 (5.48) | 1.0949 (5.48) | 1.0950 (5.48) |
| Silica filler | 0.5696 (2.85) | 0.5695 (2.85) | 0.5695 (2.85) | 0.5694 (2.85) | 0.5699 (2.85) | 0.5699 (2.85) | 0.5698 (2.85) | 0.5695 (2.85) | 0.5690 (2.85) |
| Zirconia filler | 0.3061 (1.53) | 0.3063 (1.53) | 0.3061 (1.53) | 0.3069 (1.53) | 0.3060 (1.53) | 0.3066 (1.53) | 0.3070 (1.54) | 0.3061 (1.53) | 0.3062 (1.53) |
| Zr/Si filler | 12.6295 (63.13) | 12.6249 (63.16) | 12.6288 (63.15) | 12.6268 (63.11) | 12.6280 (63.11) | 12.6263 (63.11) | 12.6280 (63.15) | 12.6309 (63.16) | 12.6270 (63.17) |

Test Results for Examples 13-20

| Example | DTS (MPa) (Std. Dev.) | Contrast Ratio | Depth of cure (mm) | Contrast Ratio/Depth of Cure | Extrusion force (Max Load, KgF) (Std. Dev.) |
|---|---|---|---|---|---|
| Control | 73.154 (3.662) | 39.03 | 5.41 | 7.21 | 11.664 (1.916) |
| 13 | 69.089 (3.227) | 56.48 | 4.33 | 13.04 | 8.999 (1.717) |
| 14 | 63.302 (2.191) | 61.56 | 3.71 | 16.59 | 10.243 (1.044) |
| 15 | 54.741 (2.737) | 66.07 | 3.36 | 19.66 | 7.254 (0.856) |
| 16 | 50.797 (3.942) | 67.52 | 3.13 | 21.57 | 7.749 (1.601) |
| 17 | 70.028 (3.04) | 36.07 | 6.07 | 5.94 | 3.609 (0.336) |
| 18 | 66.279 (3.841) | 42.35 | 5.10 | 8.30 | 2.203 (0.309) |
| 19 | 64.702 (2.692) | 59.59 | 3.79 | 15.72 | 2.616 (0.327) |
| 20 | 56.552 (1.606) | 66.59 | 3.35 | 19.87 | 2.580 (0.268) |

Polymerizable Resin Composition Example 21A

| Resin composition, grams, (wt % of resin, wt % of total composition including filler) | |
|---|---|
| Stearyl methacrylate | 0.9960 (4.97, 1.33) |
| Trimer | 5.7543 (28.72, 7.67) |
| ERGP-IEM | 11.6910 (58.34, 15.59) |
| DDMA | 1.2117 (6.05, 1.62) |
| BHT | 0.0023 (0.01, 0.003) |
| AFM-1 | 0.3027 (1.51, 0.40) |
| CPQ | 0.0142 (0.07, 0.02) |
| EDMAB | 0.0419 (0.21, 0.06) |
| DPIHFP | 0.0252 (0.13, 0.03) |

Dental Restoration Composition 21B

| Component | Comparative paste |
|---|---|
| Resin mixture | 6.6874 (26.72) |
| YbF$_3$ | 1.3807 (5.52) |
| Silica filler | 0.7225 (2.89) |

-continued

| Component | Comparative paste |
|---|---|
| Zirconia filler | 0.3931 (1.57) |
| Zr/Si filler | 15.8478 (63.31) |

The paste composition was formed into a 1 mm thick disk by placing the composite paste between two pieces of Mylar film spaced 1 mm apart and curing for 20 seconds with an LED array. Transmission electron microscopy was used to generate the image shown as FIG. 1, which shows the phase separated domains of stearyl methacrylate as lighter circular areas.

What is claimed is:

1. A method of making a dental composition comprising:
providing a hardenable dental composition comprising a polymerizable resin composition and at least 50 wt-% of inorganic oxide filler, wherein the dental composition exhibits tackiness or stringiness when manipulated with a dental instrument; and
adding fatty mono(meth)acrylate monomers in an amount ranging from 0.2 to 10 wt-% of the hardenable dental composition, wherein the fatty mono(meth)acrylate monomer phase separates from the polymerizable resin composition such that the fatty mono(meth)acrylate forms microscopic domains such that the tackiness or stringiness is substantially reduced.

2. The method of the claim 1 wherein the fatty mono (meth)acrylate monomer comprises an alkyl group having greater than 12 carbon atoms.

3. The method of the claim 1 wherein the fatty mono (meth)acrylate monomer comprises an alkyl group having 6 to 12 carbon atoms.

4. The method of claim 1 wherein the hardenable dental composition comprises at least 50 wt-% of inorganic oxide filler that comprises nanoparticles of silica, zirconia, or mixtures thereof.

5. The method of claim 4 wherein the nanoparticles are in the form of nanoclusters.

6. The method of claim 4 wherein hardenable dental composition can be extruded through an orifice with a force no greater than 20 kg for an orifice diameter of 2 mm.

7. The method of claim 1 wherein the fatty mono(meth) acrylate increases the contrast ratio of the hardenable dental composition by at least 5.

8. The method of claim 1 wherein the hardenable dental composition has a contrast ratio of at least 45 and is free of opacifying pigment.

9. The method of claim 1 wherein the hardenable dental composition has a ratio of contrast ratio to depth of cure of at least 10.

10. The method of claim 1 wherein the polymerizable resin composition comprises one or more ethylenically unsaturated monomers selected from the group consisting of isocyanurate monomers, ethoxylated resorcinol monomers, and mixtures thereof.

11. The method of claim 1 wherein the polymerizable resin composition comprises an addition-fragmentation agent.

12. The method of claim 1 wherein the polymerizable resin composition comprises at least one monomer selected from the group consisting of ethoxylated bisphenol A dimethacrylate (BisEMA6), bisphenol A diglycidyl dimethacrylate (bisGMA), urethane dimethacrylate (UDMA), and polyethyleneglycol dimethacrylate (PEGDMA).

* * * * *

UNITED STATES PATENT AND TRADEMARK OFFICE
CERTIFICATE OF CORRECTION

PATENT NO.       : 9,433,563 B2
APPLICATION NO.  : 14/111376
DATED            : September 6, 2016
INVENTOR(S)      : Bradley Craig Page 1 of 1

It is certified that error appears in the above-identified patent and that said Letters Patent is hereby corrected as shown below:

In the Specification

Column 7
Line 27, Delete "iscosyanurate" and insert -- isocyanurate --, therefor.

Column 9
Line 17, Delete "polyethylenegylcol" and insert -- polyethyleneglycol --, therefor.

Column 9
Line 20, Delete "methaycrylated" and insert -- methacrylated --, therefor.

Column 24
Lines 23-24, Delete "triethlyene" and insert -- triethylene --, therefor.

Column 24
Line 25, Delete "dodecandiol" and insert -- dodecanediol --, therefor.

Column 25
Lines 54-55, Delete "tetrafluoroboarate" and insert -- tetrafluoroborate --, therefor.

Column 33
Line 15, Delete "Alpha" and insert -- Alfa --, therefor.

In the Claims

Column 44
Line 58, In Claim 2, before "claim" delete "the".

Column 44
Line 61, In Claim 3, before "claim" delete "the".

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*